US008541173B2

(12) United States Patent
Baban et al.

(10) Patent No.: US 8,541,173 B2
(45) Date of Patent: Sep. 24, 2013

(54) ENDOMETRIOSIS-RELATED MARKERS AND USES THEREOF

(75) Inventors: Soheyl Baban, Montréal (CA); Monique Bernard, Boucherville (CA); Elana Cherry, Montréal (CA); Diane Gosselin, Pointe Calumet (CA); Patrice Hugo, Laval (CA); Brigitte Malette, Montréal (CA); Pierre Miron, Laval (CA); Charles Privé, Montréal (CA); Kamran Shazand, Verdun (CA)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 13/403,903

(22) Filed: Feb. 23, 2012

(65) Prior Publication Data
US 2012/0208869 A1    Aug. 16, 2012

Related U.S. Application Data

(62) Division of application No. 10/920,152, filed on Aug. 17, 2004, now Pat. No. 8,148,061, which is a division of application No. 09/794,928, filed on Feb. 26, 2001, now Pat. No. 6,777,182.

(60) Provisional application No. 60/185,063, filed on Feb. 25, 2000, provisional application No. 60/225,745, filed on Aug. 17, 2000.

(51) Int. Cl.
*C12Q 1/68*    (2006.01)
*C12P 19/34*    (2006.01)
*C07H 21/02*    (2006.01)

(52) U.S. Cl.
USPC .......... 435/6.17; 435/7.1; 435/91.2; 536/23.1

(58) Field of Classification Search
None
See application file for complete search history.

(56) References Cited

U.S. PATENT DOCUMENTS 6,586,569 B1    7/2003    Starzinski-Powitz et al.

FOREIGN PATENT DOCUMENTS

| DE | 198 24 230 A1 | 2/1999 |
| WO | 95/13821 | 5/1995 |
| WO | 99/63115 | 12/1999 |
| WO | 99/63116 | 12/1999 |

OTHER PUBLICATIONS

Anderson, M. J., et. al., "Cloning and Characterization of Three Human Forkhead Genes That Comprise an FKHR-like Gene Subfamily", Genomics, 47:187-199 (1998).
Baranova, H., et. al., "Possible involvement of arylamine N-acetytransferase 2, glutathione S-transferase M1 and T1 genes in the development of endometriosis", Molecular Human Reproduction, 5(7):636-641 (1999).
Barr, F., "Chomosomal Translocations Involving Paired Box Transcription Factors in Human Cancer", Int. J. Biochem. Cell Biol., 29(12):1449-1461 (1967).
Bergvist, A., et. al., "A comparison of cathepsin D levels in endometriotic tissue and in uterine endometrium", Fertility and Sterility, 62(6):1130-1134 (1996).
Biggs III, W. H., et. al., "Protein kinase B/Akt-mediated phosphorylation promotes nuclear exclusion of the winged helix transcription factor FKHR1", Proc. Natl. Acad. Sci. USA, 96:7421-7426 (Jun. 1999).
Davies, K. J. A., "The Broad Spectrum of Responses to Oxidants in Proliferating Cells: A New Paradigm for Oxidative Stress", IUBMB Life, 48:41-47 (1999).
Huang, J. C., et. al., "Quantitative Analysis of Epidermal Growth Factor Receptor Gene Expression in Endometriosis", J. of Clinical Endocrinology and Metabolism, 79(4):1097-1101 (1994).
International Search Report published with International Publication No. WO01/06259 A1 on Jan. 25, 2001.
Ishikawa, M., et. al., "Clinical Significance of Manganese Superoxide Dismutase in Ovarian Carcinoma", Acta Obst. Gynaec. Jpn., 43(5):509-515 (1991).
Jones, R. K., et. al., "Apoptosis and bcl-2 expression in normal human endometrium, endometriosis and adenomyosis", Human Reproduction, 13(12):3496-3502 (1998).
Kitawaki, J., et. al., "Expression of Aromatase Cytochrome P450 Protein and Messenger Ribonucleic Acid in Human Endometriotic and Adenomyotic Tissues but Not in Normal Endometrium", Biology of Reproduction, 57:514-519 (1997).
Knapen, M., et. al., "Glutathione and glutathione-related enzymes in reproduction: A review", European J. of Obstetrics & Gynecology and Reproductive Biology, 82:171-184 (1999).
Liang, P., et. al., "Differential Display Methods and Protocols", Methods in Molecular Biology, vol. 85, Liang, et. al., eds., Humana Press, Totowa, New Jersey, pp. 1-11(1997).
Malette, B., et. al., "Large scale validation of human N-myc Downstream-Regulated Gene (NDRG)-1 expression in endometrium during the menstrual cycle", Molecular Human Reproduction, 9(11):671-679 (2003).
Marions, L., et. al., "Expression of cyclo-oxygenase in human endometrium during the implantation period", Molecular Human Reproduction, 5(10):961-965 (1999).
Matsuda, S., et. al., "Molecular cloning and characterization of a novel human gene (HERNA) which encodes a putative RNA-helicase", Biochimica et Biophysica Acta 1490:163-169 (2000).
McLaren, J., et. al., "Immunolocalization of the apoptosis regulating proteins Bcl-2 and Bax in human endometrium and isolated peritoneal fluid macrophages in endometriosis", Human Reproduction, 12(1):146-152 (1997).

(Continued)

*Primary Examiner* — Robert Mondesi
*Assistant Examiner* — MD. Younus Meah
(74) *Attorney, Agent, or Firm* — Joseph E. Mueth

(57) ABSTRACT

The present invention relates to markers of endometriosis which are differentially expressed in the endometrial cells of females with endometriosis compared to endometriosis-free females. The invention also relates to methods for determining likelihood of endometriosis in female subjects, to methods for grading endometriosis in females suffering from endometriosis and to methods for treating this disease. The invention is also concerned with polynucleotides, probes, primers and kits useful for reducing into practice the above-mentioned methods which are more rapid, non invasive, much less complicated and much less costly than laparoscopy.

3 Claims, No Drawings

(56) References Cited

OTHER PUBLICATIONS

Meresman, G. F., et. al., "Apoptosis and expression of Bcl-2 and Bax in eutopic endometrium for women with endometriosis", Fertility and Sterility, 74(4):760-766 (Oct. 2000).

Misao, R., et. al., "Levels of sex hormone-binding globulin (SHBG) and corticosteriod-binding globulin (CBG) messenger ribonucleic acid (mRNAs) in ovarian endometriosis", Reprod. Nutr. Dev., 35:155-165 (1995).

Mori, H., et. al., "Expression of cytokine genes in peritoneal macrophages from patients with pelvic endometriosis", Japanese J. of Inflammation, 13(4):355-364 (Jul. 1993).

Ohwada, M., et. al., "Glutathione Peroxidase Activity in Endometrium: Effects of Sex Hormones and Cancer", Gynecologic Oncology, 60:277-282 (1996).

Ota, H., et. al., "Distribution of heat shock proteins in eutopic and ectopic endometrium in endometriosis and adenomyosis", Fertility and Sterility, 68(1):23-28 (Jul. 1997).

Ota, H., et. al., "Endothelial nitric oxide synthase in the endometrium during the menstrual cycle in patients with endometriosis and adenomyosis", Fertility and Sterility, 69(2):303-308 (Feb. 1998).

Ota, H., et. al., "Endometriosis and Free Radicals", Gynecologic and Obstetric Investigation, 48(suppl 1):29-35 (1999).

Ota, H., et. al., "Immunohistochemical assessment of superoxide dismutase expression in the endometrium in endometriosis and adenomyosis", Fertility and Sterility, 72(1):129-134 (Jul. 1999).

Ota, H., et. al., "Aberrant expression of glutathione peroxidase in eutopic and ectopic endometrium in endometriosis and adenomyosis", Fertility and Sterility, 74(2):313-318 (Aug. 2000).

Regidor, P.-A., et. al., "Aberrant expression pattern of gap junction connexins in endometriotic tissue", Molecular Human Reproduction, 3(5):375-381 (1997).

Sanfujinka, S., "Update", World of Obstetrics and Gynecology, 50:59-70 (1998).

Suzmori, N., et. al., "Expression of endometriosis-related gene", Treatment of Obstetrics and Gynecology, 78:492 (1998).

Vaskivuo, T.E., et. al., "Apoptosis and apoptosis-related proteins in human endometrium", Molecular and Cellular Endocrinology, 165:75-83 (2000).

ENDOMETRIOSIS-RELATED MARKERS AND USES THEREOF

This application is a divisional patent application of U.S. patent application Ser. No. 10/920,152, filed Aug. 17, 2004, now U.S Pat. No. 8,148,061, which is a divisional patent application of U.S. patent application Ser. No. 09/794,928, flied Feb. 26, 2001 and now issued as U.S. Pat. No. 6,777,182 B2, which claims the benefit of U.S. provisional applications No. 60/185,063 filed on Feb. 25, 2000 and No. 60/225,745 flied on Aug. 17, 2000. The disclosures of all of the above-identified patent applications are expressly incorporated herein by reference.

BACKGROUND OF THE INVENTION a) Field of the Invention

This is a non-provisional application of U.S. provisional applications No. 60/185,063 filed on Feb. 25, 2000 and No. 60/225,062 filed on Aug, 17, 2000.

The entire content of a Sequence Listing titled "Sequence_Listing.txt," created on Apr. 23, 2012 and having a size of 9 kilobytes, which has been submitted in electronic form in connection with the present application, is hereby incorporated by reference herein in its entirety.

The present invention relates to markers of endometriosis and more particularly to methods for determining likelihood of endometriosis in female subjects, to methods for grading endometriosis in females suffering from endometriosis and to methods for treating this disease. The invention is also concerned with polynucleotides, probes, primers and kits useful for reducing into practice the above-mentioned methods.

b) Brief Description of the Prior Art

Endometriosis is one of the most common gynecological disorders, affecting up to 10-15% of women of reproductive age. It is mainly associated with severe pelvic pain and/or infertility, but also with dysmenorrhea, dyspareunia, and several other symptoms such as intraperitoneal bleeding, back pain, constipation and/or diarrhea. Endometriosis is characterized by the implantation and growth of endometrial cells (which normally constitute the lining of the uterus) in extra-uterine sites, most frequently in the peritoneal cavity. The severity of the disease can be graded. According the American Society of Reproductive Medicine (ASRM), the disease is classified in four stages, namely, minimal (stage I), mild (stage II), moderate (stage III), and severe (stage IV). Although the etiology and pathogenesis of endometriosis remain unclear, the theory of retrograde menstruation is the most widely accepted to explain the presence of endometrial cells in ectopic sites. However, retrograde menstruation occurs in most women. Thus, a certain genetic potential or predisposition, present in the endometrial cells, might be responsible for the presence of the disease. Initially, this genetic potential may relate to mutations in the genome, but in addition, it may also lead to subsequent altered gene expression.

At present, direct visualization of the endometriotic lesions under surgical procedures (laparoscopy or laparotomy) is the only reliable method to diagnose endometriosis. However, this method is highly invasive (i.e. surgery under general anesthesia) and costly. The period of time between the onset of symptoms and disease diagnosis can be as long as 8 to 12 years. Ideally, the prospect to diagnose endometriosis more easily, rapidly, and as early as possible during the course of the disease would definitely reduce the number of years during which patients endure pain, infertility or other symptoms.

Based on this perspective, several investigators have sought to identify biological markers (proteinic and genetic) that could efficiently be used as predictive tools for endometriosis. However, to date, no one has been able to do so.

For instance, several proteins have also been shown to be differentially expressed in endometriosis. These include the tissue inhibitor of metaloproteinase-1 (TIMP-1), $\alpha_v\beta_3$ integrin, MCP-1, aromatase P450 and plasminogen activator-receptor and inhibitors. Unfortunately, the clinical relevance of these markers is uncertain since diagnostic parameters such as sensitivity and specificity of these candidate markers are still poorly defined.

Bcl-2 has been reported to be upregulated during the proliferative phase of the ovarian cycle in the eutopic endometrium of diseased women (Meresman et al. (2000) Fertil. Steril. 74(4): 760-6) as well as in endometriotic lesions in both phases of the cycle (Jones et al. (1998) Hum. Reprod. 13(12): 3496-502) and in macrophages from the peritoneal fluid of women having endometriosis (McLaren et al. (1997) Hum. Reprod. 12(1): 146-52). However, these results differ from our data presented herein in which a downregulation of Bcl-2 is observed in the eutopic tissue of women with endometriosis compared to disease-free women, independent of the phase of the ovarian cycle.

Connexin 43 (Cx43), a protein involved in gap junctions, has been reported to be aberrantly expressed in the glandular uterine epithelium of ectopic endometrial tissue in women with endometriosis (Regidor et al (1997) Mol. Hum. Reprod. 3:375-381). The goal of this study was solely to determine the hormonal regulation of connexins in endometriotic tissues, and consequently, this report did not analyze eutopic tissue in either women with endometriosis nor in disease-free women. Thus, findings in this study have little clinical or diagnostic relevance.

Human cyclooxygenase-2 (COX-2) is involved in prostaglandin synthesis, and, as a result, has been implicated in the growth and differentiation of endometrial stromal cells as well as during the implantation period necessary to establish pregnancy (Marions and Danielsson (1999) Mol. Hum. Reprod. 5:961-5). Due to its role in implantation during pregnancy, it has been postulated that COX-2 may be involved in the implantation of endometrial cells in ectopic sites, giving rise to endometriosis. However, to date, there have not been any conclusive reports demonstrating the role of COX-2 in endometriosis, nor that an alteration of its expression leads to the disease.

An increase in the expression at the protein level of heat shock protein 70 (HSP70) has been described in endometrial glandular cells of women having endometriosis and adenomyosis compared to a control group (Ota et al. (1997) *Fertil Steril* 68: 23-28). This result was obtained by immuno-histochemistry. The same authors using the same technique showed that endothelial nitric oxide synthase (eNOS) and superoxide dismutase (SOD) were also up-regulated in the endometrium of patients with endometriosis or adenomyosis (Ota et al. (1998) *Fertil Steril* 69: 303-308; Ota et al. (1999) *Fertil Steril* 72: 129-134). However, these studies have limited clinical value because some of the experiments were not always carried out with an accurate technical approach, and because the markers were tested on a small number of patients yielding no statistically significant results. Furthermore, in Ota's studies, altered gene expression was found to occur in the ectopic tissue, as opposed to in the eutopic endometrium, and the results presented are therefore not industrially applicable.

Others groups studying gene expression have reported that the gluthatione S-transferase (GST) gene had a higher degree of polymorphism in endometriosis compared to a control group, and therefore represented an overall less-performing detoxification system which predisposed women to the disease (Baranova et al., (1999) Mol. Hum. Reprod. 5:636-641). These results reflect a genetic predisposition to have the disease rather than the likelihood of endometriosis.

Overall, no one has ever described any, methods for determining the likelihood of endometriosis in females, any methods for efficiently identifying females suffering from endometriosis, nor any methods for grading endometriosis in females suffering from the disease.

There is therefore a need for an alternative approach to laparoscopy or laparotomy to diagnose and determine the stage of endometriosis. More particularly, it would be highly desirable to be provided with methods wherein endometrial cells samples are assayed for expression levels of specific endometriosis-related genes (RNA or cDNA transcripts or their corresponding proteins), that are known to be differentially expressed in the endometrial cells of females with endometriosis (Endo group) compared to endometriosis-free females (Control group).

The present invention fulfils these needs and also other needs which will be apparent to those skilled in the art upon reading the following specification.

SUMMARY OF THE INVENTION

One aim of the present invention is to provide a method for determining the likelihood of endometriosis in female subjects.

The present invention also aims to provide a method for grading endometriosis in females suffering from this disease, as well as a method for treating this disease.

The invention is also concerned with primers, probes and kits useful for reducing into practice the above-mentioned methods.

In accordance with an aspect of the present invention, there is provided a method for determining the likelihood of endometriosis in female subjects whereby expression levels of one or more selected endometriosis-related marker(s) is assayed, and the expression level of the marker is indicative of the likelihood of endometriosis in the subject. In a preferred embodiment, the endometriosis-related marker(s) is selected from the group consisting of:
  i) genes selected from the group consisting of the genes listed in TABLE 1 for which a GENBANK™ gene name is given;
  ii) ribonucleic acids selected from the group consisting of:
    a) ribonucleic acids giving rise to cDNAs selected from the group consisting of: cDNAs derived from genes defined in i); and cDNAs comprising a sequence selected from SEQ ID NOs: 1 to 16; and
    b) fragments of the ribonucleic acids defined in a); and
  iii) peptides or proteins encoded by the genes defined in i), or encoded by the ribonucleic acids defined in ii).

In another aspect, the present invention relates to the used of OXPHOS-endometriosis-related markers in a method for determining likelihood of endometriosis in a female subject. This method comprises the steps of:
  obtaining a sample of eutopic endometrial cells, preferably epithelial endometrial cells, from the female subject;
  assaying the endometrial cells sample for the expression level of at least one endometriosis-related marker involved in the oxidative phosphorylation pathway and/or the internal redox potential sensors pathway (OXPHOS) of the endometrial cells;
  determining likelihood of endometriosis in the female subject by comparing the expression level for the at least one OXPHOS-endometriosis-related marker to an established baseline level for the at least OXPHOS-endometriosis-related marker.

In a further aspect, the present invention relates to the assay of nucleic acid product(s) of endometriosis-related marker(s) in methods for determining likelihood of endometriosis in a female subject. This method comprises the steps of:
  obtaining a sample of endometrial cells, preferably eutopic endometrial cells, from the female subject;
  assaying the endometrial cells sample for the expression level of at least one nucleic acid product of an endometriosis-related marker selected from the group consisting of:
    i) genes selected from the group consisting of the genes listed in TABLE 1 for which a (GENBANK™ gene name is given;
    ii) ribonucleic acids selected from the group consisting of:
      a) ribonucleic acids giving rise to cDNAs selected from the group consisting of: cDNAs derived from genes defined in i); and cDNAs comprising a sequence selected from SEQ ID NOs: 1 to 16; and
      b) fragments of the ribonucleic acids defined in a);
  and
  determining likelihood of endometriosis in the female subject by comparing the expression level of said at least one nucleic acid product to an established baseline level.

In another aspect, the present invention relates to the assay of protein product(s) of endometriosis-related marker(s) in methods for determining likelihood of endometriosis in a female subject. This method comprises the steps of:
  obtaining a sample of endometrial cells, preferably eutopic endometrial cells, from the female subject;
  assaying this endometrial cells sample for the expression level of at least one protein product of an endometriosis-related marker or of least one fragment of this protein product, the at least one endometriosis-related marker being selected from the group consisting of:
    i) genes selected from the group consisting of the genes listed in TABLE 1 for which a GENBANK™ gene name is given;
    ii) ribonucleic acids selected from the group consisting of:
      a) ribonucleic acids giving rise to cDNAs selected from the group consisting, of: cDNAs derived from genes defined in i); and cDNAs comprising a sequence selected from SEQ ID NOs: 1 to 16; and
      b) fragments of the ribonucleic acids defined in a);
  and
  determining likelihood of endometriosis in the female subject by comparing the expression level of the at least one protein product to an established baseline level.

According to another aspect, the present invention relates to a method for grading endometriosis. This method comprises the steps of:
  obtaining a sample of endometrial cells, preferably eutopic endometrial cells, from a female subject suffering from endometriosis; and
  assaying said endometrial cells sample for the expression level of at least one endometriosis-related marker selected from the group consisting of:
    i) genes selected from the group consisting of RNA helicase, NADH dehydrogenase, hUCC1, AK3, GST, 12S rRNA, CO2, aconitase, c-jun, Cx43, GPx4, cox2, hUCC1, Glut-1, T1227H, IL-1β, HSP 90;
ii) ribonucleic acids selected from the group consisting of:
   a) ribonucleic acids giving rise to cDNAs selected from the group consisting of: cDNAs derived from genes defined in i); and cDNAs comprising a sequence selected from SEQ ID NO: 1, SEQ ID NO: 6, SEQ ID NO: 8, SEQ ID NO 10 and SEQ ID NO 13; and
   b) fragments of the ribonucleic acids defined in a); and
iii) peptides or proteins encoded by the genes defined in i), or encoded by the ribonucleic acids defined in ii);
the expression level of the at least one endometriosis-related marker being indicative of the stage of endometriosis in the female subject.

According to another aspect, the present invention relates to a kit for determining likelihood of endometriosis in a female subject or for grading endometriosis in a female subject suffering from endometriosis. The kit comprises at least one binding molecule for binding to nucleic acid product(s) or protein product(s) of endometriosis-related marker(s). According to a preferred embodiment, the binding molecule binding molecule is a nucleic acid. In another preferred embodiment, the binding molecule is an isolated antibody.

According to a further aspect, the present invention relates isolated polynucleotides, primers and/or probes and to their uses in methods for determining likelihood of endometriosis in a female subject or for grading endometriosis in a female subject suffering from endometriosis.

The present invention also relates to a method for treating endometriosis comprising the step of modulating expression level of at least one selected endometriosis-related marker.

An advantage of the present invention is that it is rapid, non-invasive, and significantly less complicated and costly than performing laparoscopy or laparotomy. In contrast to currently-available methods, it is possible, according to the present invention, to directly measure expression levels of endometriosis-related genes that are expressed differentially in endometrial cells depending of the presence/absence of endometriosis and the stage of the disease with relatively high levels of sensitivity and specificity.

Other objects and advantages of the present invention will be apparent upon reading the following non-restrictive description.

DETAILED DESCRIPTION OF THE INVENTION

A) Definitions

Throughout the text, the words "base pairs" are generally abbreviated as "bp", the words "deoxyribonucleic acid" as "DNA", the words "ribonucleic acid" as "RNA", the words "complementary DNA" as "cDNA", the words "polymerase chain reaction" as "PCR", and the words "reverse transcription" as "RT". Nucleotide sequences are written in the 5' to 3' orientation unless stated otherwise.

In order to provide an even clearer and more consistent understanding of the specification and the claims, including the scope given herein to such terms, the following definitions are provided:

Binding molecule: Any molecule which adheres to a given target molecule in a adequate manner, for example, enzymes to substrates, antibodies to antigens, or a DNA strand to its complementary strand.

Derived from: As used herein, a cDNA "derived from" a gene when this cDNA has been synthesized from a messenger RNA coded by this gene.

Typically, cDNAs are synthesized in an in vitro reaction catalyzed by a viral reverse transcriptase in which a complementary strand of DNA is produced from an isolated mRNA template.

Endometrial cells: Refer to the cells which form the tissue lining the uterus (stromal and epithelial cells). Normally, endometrial cells are sloughed off during the woman's menstrual period, and afterwards grows back and slowly thickens until the next period. As used herein, "endometrial cells" encompasses eutopic as well as ectopic endometrial cells, where endometrial cells that usually constitute the lining of the uterine cavity are considered eutopic, and those outside the uterus are considered ectopic.

Endometriosis-related marker: Refers to any amino acid product or nucleic acid product for which the level of expression in the endometrium of a female is correlated with endometriosis.

Expression level: Refers to the amount of a definite amino acid product or of a definite nucleic acid product in a given cell or tissue. "Expression" more particularly refers to the process by which a gene coded information is converted into the structures present and operating in the cell. As used herein, expressed genes include those that are transcribed into mRNA and then translated into protein and those that are transcribed into RNA but not translated into protein (for example, transfer and ribosomal RNAs). Similarly, the expression "baseline expression level" refers to the level of expression which is found under normal conditions and normal level of functioning (e.g. endometriosis-free female). The terms "overexpression" and "underexpression" refer to an upward or a downward deviation respectively in assayed levels of expression as compared to the baseline expression level.

Female subject: Refers to human females being in reproductive age.

According to the present invention, the female subject would preferably presents clinical symptoms of endometriosis such as infertility and pelvic pain.

Fragment: Refers to a section of a molecule, such as a protein or a nucleic acid, and is meant to refer to any portion of the amino acid or nucleotide sequence.

Gene: Refers to a DNA sequence related to a single polypeptide chain or protein, and as used herein includes the 5' and 3' untranslated regions.

Giving rise to: As used herein, a ribonucleic acid "gives rise to" a cDNA when it serves as a template for synthesizing the cDNA. Typically, cDNAs are synthesized in an in vitro reaction catalyzed by a viral reverse transcriptase in which a complementary strand of DNA is produced from an isolated mRNA template.

Likelihood: As used herein in combination with the term "endometriosis", it more particularly refers to an existing probability of a female subject of really suffering from endometriosis. It does not refer to a predisposition to suffering in the future from the disease.

Nucleic acid product: Any molecule having one or more nucleotide(s) derived from the expression of gene. As used herein in combination with the expression "endometriosis-related marker", it more particularly refers to RNA and fragments thereof, cDNAs and fragments thereof, and expressed sequence tags (ESTs) which expression is correlated with the expression of an endometriosis-related marker (see hereinbefore).

OXPHOS: Abbreviation for "oxidative phosphorylation". As used herein, it refers to the sequence of enzymatic reactions coupled to the mitochondrial respiratory chain whereby ATP is phosphorylated, as well as to the nucleic acid and protein products involved in these reactions.

Phase of estrous cycle: refers to the period of estrus in which physiological changes occur in females as a result of hormonal influences during the menstrual or ovarian cycle. Briefly, In human females, the menstrual cycle is divided into two phases, namely, the "proliferative phase" (also called the follicular phase, herein referred to as P phase) and the "secretory phase" (also called the luteal phase, herein referred to as S phase). The proliferative phase normally extends from day 0 to day 14 of the menstrual cycle, and the secretory phase normally extends from day 15 to day 28, where ovulation occurs on day 14 of a standard menstrual cycle.

Protein product refers to organic molecules that contain two or more amino acids which are assembled by formation of peptide bonds during ribosomal translation of a messenger RNA. As used herein in combination with the expression "endometriosis-related marker", it more particularly refers to peptides, proteins, glycoproteins, and protein fragments whose expression is correlated with the expression of an endometriosis-related marker (see hereinbefore).

B) General Overview of the Invention

The present invention concerns the early detection, diagnosis, prognosis, grading and treatment of endometriosis. Markers of endometriosis in the form of nucleic acid sequences, proteins and peptides isolated from human endometrial cells are disclosed. Levels of expression of these "endometriosis-related markers" are indicative of the likelihood of endometriosis in a female subject and of the stage of endometriosis in a female subject diagnosed as having endometriosis. Preferably, the endometriosis-related markers of the invention are those listed in Table 1 hereafter. Table 2 lists the nucleotide sequences of some of these endometriosis-related markers, also referred by the inventors as DD1 to DD16 (SEQ ID NOs: 1 to 16).

C) Methods for Determining the Likelihood of Endometriosis i) Endometriosis-Related Markers According to an aspect of the invention, the endometriosis-related markers are used in a method for determining the likelihood of endometriosis in a female subject. This method comprises the steps of:

obtaining a sample of endometrial cells from a female subject (preferably eutopic endometrial cells, and even more preferably epithelial eutopic endometrial cells);

assaying the endometrial cells sample for the expression level of at least one endometriosis-related markers selected from the group consisting of:
i) genes selected from the group consisting of the genes listed in TABLE 1 for which a GENBANK™ gene name is given;
ii) ribonucleic acids selected from the group consisting of:
a) ribonucleic acids giving rise to cDNAs selected from the group consisting of: cDNAs derived from genes defined in i); and cDNAs comprising a sequence selected from SEQ ID NOs: 1 to 16; and
b) fragments of the ribonucleic acids defined in a); and
iii) peptides or proteins encoded by the genes defined in i), or encoded by the ribonucleic acids defined in ii).

According to this method, the expression level of the endometriosis-related marker(s) is indicative of the likelihood of endometriosis in the female subject. Preferably, the method further comprises the step of comparing the expression level for the endometriosis-related marker to an established baseline expression level. The baseline level for the endometriosis-related marker(s) is preferably established by assaying the expression level for the same marker(s) in a negative reference group of endometriosis-free women.

According to a preferred embodiment, overexpression of at least one endometriosis-related marker listed in Table 4 is indicative of a higher likelihood of endometriosis in the female subject, and more particularly, the following endometriosis-related markers:
i) genes selected from the group consisting of: NADH dehydrogenase, hUCC1, Paralemmin, citrate transport protein, HIF1α, ARNT, Glut-1, MnSOD, GPx, ATP synthase, c-jun, Cx43, HSP 70, and cox2;
ii) ribonucleic acids selected from the group consisting of:
a) ribonucleic acids giving rise to cDNAs selected from the group consisting of: cDNAs derived from genes defined in i); and cDNAs comprising a sequence selected from SEQ ID NO: 9, SEQ ID NO: 10, SEQ ID NOs: 13 to 15; and
b) fragments of the ribonucleic acids defined in a); and
iii) peptides or proteins encoded by the genes defined in i), or encoded by the ribonucleic acids defined in ii);

According to another preferred embodiment, underexpression of at least one endometriosis-related marker listed in Table 5 is indicative of a higher likelihood of endometriosis in the female subject, and more particularly, the following endometriosis-related markers:
i) genes selected from the group consisting of: Cap43, RNA helicase, CO3, FKHR, 12S rRNA, AK3, catalase, GST, eNOS, 12S rRNA, T1227H, CO2, aconitase, ANT-1, Bcl-2, COUP-TF, IL-1β, HSP 90, GPx4, and GRP78;
ii) ribonucleic acids selected from the group consisting of:
a) ribonucleic acids giving rise to cDNAs selected from the group consisting of: cDNAs derived from genes defined in i); and cDNAs comprising a sequence selected from SEQ ID NOs: 1 to 8, SEQ ID NO 11, SEQ ID NO 12, and SEQ ID NO 16; and
b) fragments of the ribonucleic acids defined in a); and
iii) peptides or proteins encoded by the genes defined in i), or encoded by the ribonucleic acids defined in ii).

The inventors have also found that some endometriosis-related markers are modulated depending on whether endometrial cells are obtained at the proliferative phase or at the secretory phase of the estrous cycle of the female subject. Tables 6 and 7 hereafter provide a list of the endometriosis-related markers of the invention whose expression levels were found to be modulated in the proliferative and the secretory phases, respectively. Therefore, in a preferred embodiment, the method of the invention further comprises the steps of: i) defining at which phase of the estrous cycle the endometrial cells were obtained; and ii) selecting the endometriosis-related marker for which expression level is to be assayed according to the phase defined in i). The phase of the estrous cycle may be evaluated by using techniques well known in the art such as histological examination (preferably of endometrial tissues), methods for evaluating level of expression of RNA, and methods for evaluating sex steroids levels to name a few.

Therefore, in a preferred embodiment, the endometrial cells from the female subject are sampled at the proliferative phase of her estrous cycle, and overexpression level of at least one endometriosis-related marker selected from the group consisting of:
- i) genes selected from the group consisting of: NADH dehydrogenase, hUCC1, Paralemmin, citrate transport protein, HIF1α, ARNT, Glut-1, MnSOD, GPx, ATP synthase, c-jun, Cx43, HSP 70, and cox2;
- ii) ribonucleic acids selected from the group consisting of:
  - a) ribonucleic acids giving rise to cDNAs selected from the group consisting of: cDNAs derived from genes defined in i); and cDNAs comprising a sequence selected from SEQ ID NO: 9, SEQ ID NO: 10, SEQ ID NOs: 13 to 15; and
  - b) fragments of the ribonucleic acids defined in a); and
- iii) peptides or proteins encoded by the genes defined in i), or encoded by the ribonucleic acids defined in ii);

is indicative of a higher likelihood of endometriosis in said female subject as compared to an endometriosis-free female subject.

In another preferred embodiment, the endometrial cells from the female subject are sampled at the secretory phase of her estrous cycle, and overexpression level of at least one endometriosis-related marker selected from the group consisting of:
- i) genes selected from the group consisting of hUCC1, Paralemmin, citrate transport protein, HIF1α, Glut-1, MnSOD, GPx, ATP synthase, c-jun, Cx43, HSP 70, and cox2;
- ii) ribonucleic acids selected from the group consisting of:
  - a) ribonucleic acids giving rise to cDNAs selected from the group consisting of: cDNAs derived from genes defined in i); and cDNAs comprising a sequence selected from SEQ ID NOs: 13 to 15; and
  - b) fragments of the ribonucleic acids defined in a); and
- iii) peptides or proteins encoded by the genes defined in i), or encoded by the ribonucleic acids defined in ii);

is indicative of a higher likelihood of endometriosis in said female subject as compared to an endometriosis-free female subject.

Yet, in a further preferred embodiment, the endometrial cells from the female subject are sampled at the proliferative phase of her estrous cycle, and underexpression level of at least one endometriosis-related marker selected from the group consisting of:
- i) genes selected from the group consisting of: Cap43, RNA helicase, FKHR, 12S rRNA, AK3, GST, eNOS, TI227H, CO2, ANT-1, Bcl-2, IL-1β, and HSP 90;
- ii) ribonucleic acids selected from the group consisting of:
  - a) ribonucleic acids giving rise to cDNAs selected from the group consisting of: cDNAs derived from genes defined in i); and cDNAs comprising a sequence selected from SEQ ID NO: 2, SEQ ID NO 3, SEQ ID NO 5, SEQ ID NO 7, SEQ ID NO 8, SEQ ID NO 12, and SEQ ID NO 16; and
  - b) fragments of the ribonucleic acids defined in a); and
- iii) peptides or proteins encoded by the genes defined in i), or encoded by the ribonucleic acids defined in ii);

is indicative of a higher likelihood of endometriosis in said female subject as compared to an endometriosis-free female subject.

In another preferred embodiment, the endometrial cells from the female subject are sampled at the secretory phase of her estrous cycle, and underexpression level of at least one endometriosis-related marker selected from the group consisting of:
- i) genes selected from the group consisting of: RNA helicase, CO3, FKHR, 12S rRNA, AK3, catalase, GST, 12S rRNA, T1227H, aconitase, Bcl-2, COUP-TF, IL-1β, HSP 90, GPx4, and GRP78;
- ii) ribonucleic acids selected from the group consisting of:
  - a) ribonucleic acids giving rise to cDNAs selected from the group consisting of: cDNAs derived from genes defined in i); and cDNAs comprising a sequence selected from SEQ ID NOs: 1 to 8, SEQ ID NO 11, SEQ ID NO 12, and SEQ ID NO 16; and
  - b) fragments of the ribonucleic acids defined in a); and
- iii) peptides or proteins encoded by the genes defined in i), or encoded by the ribonucleic acids defined in ii);

is indicative of a higher likelihood of endometriosis in said female subject as compared to an endometriosis-free female subject.

In another preferred embodiment of the invention, the expression level of at least two endometriosis-related markers is assayed in combination. By combining markers, it is generally possible to increase the specificity and the sensitivity of the methods of the invention. Table 11 contains some examples of endometriosis-related markers combination. Methods for assaying the expression levels of genetic and proteinic markers such as the endometriosis-related markers of the present invention are well known. Methods and materials for assaying nucleic acids include: BioChips, membranes, and glass cDNA array-based techniques; RT-PCR, in situ hybridization; in vitro promoter-fusion studies in cell lines or primary culture models; transcription rate study techniques such as nuclear run-on; membrane blot hybridization approaches; direct labeling of the nucleic acids. Methods and materials for assaying proteins and peptides include: membrane blot hybridization approaches; direct labeling of the protein or peptide; proteomics; flow cytometry; immunocytochemistry; immunohistochemistry; and ELISA-based approaches. A person skilled in molecular biology and immunology will know how to select, adapt, and use these methods according to his specific need in order to obtain valuable results. For example, it could be relatively easy to develop biochips bearing genetic markers considered the best in terms of specificity and sensitivity for cDNA hybridization arrays to screen females, and more particularly females having endometriosis-related symptoms.

In some cases, overexpression of certain genetic and proteinic markers induces the production of auto-antibodies in the patients' blood. Therefore, measurement of these auto-antibodies could be another alternative, although indirect, to assay the expression levels of the genetic and proteinic markers according to the invention.

ii) OXPHOS-Endometriosis-Related Markers

In another aspect, the present invention relates to the use of OXPHOS-endometriosis-related markers in a method for determining the likelihood of endometriosis in a female subject. OXPHOS refers to the oxidative phosphorylation pathway and/or the internal redox potential sensors pathway of the endometrial cells. This method comprises the steps of:
- obtaining a sample of eutopic endometrial cells, preferably epithelial endometrial cells, from the female subject;
- assaying the endometrial cell sample for the expression level of at least one endometriosis-related marker involved in OXPHOS;
- determining the likelihood of endometriosis in the female subject by comparing the expression level for the at least one OXPHOS-endometriosis-related marker to an established baseline level for the at least OXPHOS-endometriosis-related marker.

According to a preferred embodiment, the OXPHOS-endometriosis-related marker involved in the oxidative phosphorylation pathway of the endometrial cells is a gene selected from the group consisting of NADH dehydrogenase, citrate transport protein, HIF1α, ARNT, AK3, Glut-1, MnSOD, GPx, GRP78, catalase, GST, eNOS, CO2, aconitase, ANT-1, ATP synthase, Bcl-2, GPx4, and cox2. It may also be preferable to select the OXPHOS-endometriosis-related marker to be assayed according to the phase of the estrous cycle in which the endometrial cells belong.

iii) Nucleic Acid Products of an Endometriosis-Related Marker

In another aspect, the present invention relates to assaying nucleic acid products of an endometriosis-related marker according to methods for determining the likelihood of endometriosis in a female subject. This method comprises the steps of:

obtaining a sample of endometrial cells, preferably eutopic endometrial cells, from the female subject;

assaying the endometrial cells sample for the expression level of at least one nucleic-acid product of an endometriosis-related marker selected from the group consisting of:
  i) genes selected from the group consisting of the genes listed in TABLE 1 for which a GENBANK™ gene name is given;
  ii) ribonucleic acids selected from the group consisting of:
    a) ribonucleic acids giving rise to cDNAs selected from the group consisting of: cDNAs derived from genes defined in i); and cDNAs comprising a sequence selected from SEQ ID NOs: 1 to 16; and
    b) fragments of the ribonucleic acids defined in a);

and
determining likelihood of endometriosis in the female subject by comparing the expression level of said at least one nucleic acid product to an established baseline level.

According to a preferred embodiment, the likelihood of endometriosis in the female subject is determined by assaying the level of expression of at least one nucleic acid product of a gene selected from the group consisting of: Cap43, RNA helicase, NADH dehydrogenase, CO3, FKHR, hUCC1, Paralemmin, citrate transport protein, HIF1α, ARNT, AK3, MnSOD, GPx, aconitase, ATP synthase, c-jun, COUP-TF, Cx43, HSP 70, and GRP78.

According to another preferred embodiment, the likelihood of endometriosis in the female subject is determined by assaying the level of expression of a ribonucleic acid selected from the group consisting of: ribonucleic acids giving rise to cDNAs comprising a sequence selected from SEQ ID NOs: 8 to 16 and fragments thereof.

More preferably, the baseline level of the selected endometriosis-related marker(s) is established by assaying its expression level in a negative reference group of endometriosis-free women. Preferably also, the at least one nucleic acid product is a messenger ribonucleic acid (mRNA) and this mRNA serves as a template for the synthesis of a cDNA.

The expression level of the at least one nucleic acid product can be assayed using well known methods such as biochips, membranes, and glass cDNA array-based methods; RT-PCR; in situ hybridization; in vitro promoter-fusion studies in cell lines or primary cultures; transcription rate study methods; membrane blot hybridization; and labeling. Even more preferably, the expression level for at least two endometriosis-related markers is assayed. It may also be desirable to define at which phase of the estrous cycle the endometrial cells were obtained in order to properly select the endometriosis-related marker for which a nucleic acid product to be assayed is in accordance with this phase.

iv) Protein Products of an Endometriosis-Related Marker

In another aspect, the present invention relates to assaying amino acid products of an endometriosis-related marker according to methods for determining the likelihood of endometriosis in a female subject. This method comprises the steps of:

obtaining a sample of endometrial cells, preferably eutopic endometrial cells, from the female subject;

assaying this endometrial cells sample for the expression level of at least one protein product of an endometriosis-related marker or of at least one fragment of this protein product, the at least one endometriosis-related marker being selected from the group consisting of:
  i) genes selected from the group consisting of the genes listed in TABLE 1 for which a GENBANK™ gene name is given;
  ii) ribonucleic acids selected from the group consisting of:
    a) ribonucleic acids giving rise to cDNAs selected from the group consisting of: cDNAs derived from genes defined in i); and cDNAs comprising a sequence selected from SEQ ID NOs: 1 to 16; and
    b) fragments of the ribonucleic acids defined in a);

and
determining the likelihood of endometriosis in the female subject by comparing the expression level of the at least one protein product to an established baseline level.

According to a preferred embodiment, the baseline level of the selected protein product(s) is established by assaying its expression level in a negative reference group of endometriosis-free women. Preferably also, the at least one protein product is the CAP-43 protein or a fragment thereof.

The expression level of the at least one protein product can be assayed using well known methods such as membrane blot hybridization; labeling; proteomics; flow cytometry; immunocytochemistry; immunohistochemistry and ELISA. Even more preferably, the expression level of at least two endometriosis-related markers is assayed in combination. It may also be preferable to define at which phase of the estrous cycle the endometrial cells were obtained in order to properly select the endometriosis-related marker so that the protein product to be assayed is in accordance with this phase.

D) Methods for Grading Endometriosis

The present inventors also found that the expression levels of specific endometriosis-related markers were modulated depending on the stage of the disease. Table 8 hereafter provides a list of the endometriosis-related markers whose expression levels were found to be modulated depending on the stage of the disease. Therefore, according to another aspect, the present invention relates to a method for grading endometriosis. This method comprises the steps of:

obtaining a sample of endometrial cells, preferably eutopic endometrial cells, from a female subject suffering from endometriosis; and assaying said endometrial cells sample for the expression level of at least one endometriosis-related marker selected from the group consisting of:
  i) genes selected from the group consisting of RNA helicase, NADH dehydrogenase, hUCC1, AK3, GST, 12S rRNA, CO2, aconitase, c-jun, Cx43, GPx4, cox2, hUCC1, Glut-1, T1227H, IL-1β, HSP 90;

ii) ribonucleic acids selected from the group consisting of:
   a) ribonucleic acids giving rise to cDNAs selected from the group consisting of: cDNAs derived from genes defined in i); and cDNAs comprising a sequence selected from SEQ ID NO: 1, SEQ ID NO: 6, SEQ ID NO: 8, SEQ ID NO 10 and SEQ ID NO 13; and
   b) fragments of the ribonucleic acids defined in a); and
iii) peptides or proteins encoded by the genes defined in i), or encoded by the ribonucleic acids defined in ii);
the expression level of the at least one endometriosis-related marker being indicative of the stage of endometriosis in the female subject.

In a preferred embodiment, the method is used so that the level of expression of the at least one endometriosis-related marker indicates whether the female subject is at stage I or II, or at stage III or IV of endometriosis.

More particularly, it was found that overexpression of NADH dehydrogenase, c-jun, Cx43, and/or cox2 is indicative of whether the female subject is substantially at stage I or II of endometriosis; and that overexpression of hUCC1 and/or Glut-1 is indicative of whether the female subject is at stage III or IV of endometriosis. It was also found that underexpression of CO2, SEQ ID NO:1, SEQ ID NO:6, aconitase, GPx4, RNA helicase, AK3, GST, and/or 12S rRNA is indicative of whether the female subject is substantially at stage I or II of endometriosis; and that underexpression of T1227H, IL-1β, and/or HSP 90 is indicative of whether the female subject is at stage III or IV of endometriosis. Whether these markers are underexpressed or overexpressed is thus a strong indication of the stage of the disease.

More preferably, the method further comprises the step of comparing the expression level for the at least one endometriosis-related marker to an established baseline level. The baseline level may be obtained by:
   assaying the expression level of the at least one endometriosis-related marker in a sample of endometrial cells from a first positive reference group of female subjects known to be at a substantially definite stage of endometriosis;
   assaying the expression level of the at least one endometriosis-related marker in a sample of endometrial cells from a second positive reference group of female subjects known to be at another substantially definite stage of endometriosis different from the stage of the first positive reference group; and
   comparing expression level of the at least one endometriosis-related marker with expression levels from the first and second positive reference groups.

Measurement of the expression levels of the endometriosis-related markers (genetic or protein) of the present invention can be accomplished as described herein. It may also be preferable to define at which phase of the estrous cycle the endometrial cells were obtained in order to properly select the endometriosis-related marker so that the protein product to be assayed is in accordance with this phase.

E) Kit

According to another aspect, the present invention relates to a kit for determining likelihood of endometriosis in a female subject or for grading endometriosis in a female subject suffering from the disease. The kit of the invention comprises:
at least one binding molecule for binding to a nucleic acid product or a protein product of an endometriosis-related marker, the endometriosis-related marker being selected from the group consisting of:
   i) genes selected from the group consisting of the genes listed in TABLE 1 for which a GENBANK™ gene name is given;
   ii) ribonucleic acids selected from the group consisting of:
      a) ribonucleic acids giving rise to cDNAs selected from the group consisting of: cDNAs derived from genes defined in i); and cDNAs comprising a sequence selected from SEQ ID NOs: 1 to 16; and
      b) fragments of the ribonucleic acids defined in a); and
   i) peptides or proteins encoded by the genes defined in i), or encoded by the ribonucleic acids defined in ii);
and
at least one element selected from the group consisting of: a support for the binding molecule(s), mixing tubes, buffers, enzymes, and substances for the detection of the binding molecule(s).

According to a preferred embodiment, the binding molecule is a nucleic acid hybridizing under standard conditions to a nucleic acid selected from the group consisting of:
   a) ESTs and mRNAss for which a GENBANK™ accession number is given in TABLE 1;
   b) single-stranded nucleic acids which hybridize under standard conditions to the nucleic acids defined in a);
   c) single-stranded nucleic acids obtained by reverse transcription of a nucleic acid defined in a) or b);
   d) DNAs and cDNAs for which a GENBANK™ accession number is given in TABLE 1;
   e) double-stranded and single-stranded nucleic acids which hybridize under standard conditions to the nucleic acids defined in d);
   f) double-stranded and single-stranded nucleic acids obtained by reverse transcription of a nucleic acid defined in d) or e); and
   g) fragments of the nucleic acids defined in a) to f).

As used herein, nucleic acid hybridization refers to the principle that two single-stranded nucleic acid molecules that have complementary base sequences will reform the thermodynamically favored double-stranded structure if they are mixed under proper conditions. For example, a medium stringency condition could be provided by approximately 0:1 to 0.25M NaCl at temperatures of approximately 37° C. to 55° C., while a low stringency condition could be provided by approximately 0.15 M to 0.9 M NaCl, at temperatures ranging from approximately 20° C. to 55° C. Thus, the "standard hybridization conditions" varies depending on the desired results.

According to another preferred embodiment, the binding molecule is an isolated antibody directed against at least one protein product of an endometriosis-related marker as defined previously, or directed against a fragment of the protein product(s).

Other types of binding molecules include small molecules such as sugars and glycoproteins.

F) Polynucleotides, Primers, Probes and their Uses

According to another aspect, the present invention relates to isolated polynucleotides. The polynucleotides of the invention are selected from the group consisting of:
   a) polynucleotides comprising a nucleic acid sequence selected from the group consisting of: SEQ ID NOs: 1 to 10, SEQ ID NOs: 12 to 16, and portion thereof; and
   b) polynucleotides comprising a nucleic acid sequence complementary to the polynucleotides defined in a).

These polynucleotides have many uses, particularly as biological markers according to the methods of the present invention, as primers and/or as probes for endometriosis. They could also be used as a template for preparing single-stranded or double-stranded nucleic acids useful in gene therapy methods (antisense, gene silencing, double-stranded RNA, etc).

The invention also relates to primers and/or probes for determining likelihood of endometriosis in a female subject or for grading endometriosis in a female subject suffering from endometriosis. According to the invention, the primer or the probe comprises an isolated nucleic acid selected from the group consisting of:
- a) ESTs and mRNAs for which a GENBANK™ accession number is given in TABLE 1;
- b) single-stranded nucleic acids which hybridize under standard conditions to the nucleic acids defined in a);
- c) single-stranded nucleic acids obtained by reverse transcription of a nucleic acid defined in a) or b);
- d) DNAs and cDNAs for which a GENBANK™ accession number is given in TABLE 1;
- e) double-stranded and single-stranded nucleic acids which hybridize under standard conditions to the nucleic acids defined in d);
- f) double-stranded and single-stranded nucleic acids obtained by reverse transcription of a nucleic acid defined in d) or e); and
- g) fragments of the nucleic acids defined in a) to f).

The invention also encompasses the uses of the aforementioned isolated polynucleotides and nucleic acids in methods for determining likelihood of endometriosis in a female subject or in methods for grading endometriosis in a female subject suffering from endometriosis. These methods may include the use of biochips, membranes, and glass cDNA array-based techniques; RT-PCR; in situ hybridization; in vitro promoter-fusion studies in cell lines or primary cultures; transcription rate study methods; membrane blot hybridization; and labeling. For instance, some of the isolated nucleic acids described above considered "the best" in terms of specificity and sensitivity to screen females could be coupled to a biochip for screening females for endometriosis and/or for evaluating the stage of her disease.

The invention also includes diagnostic method for the detection of endometriosis in a female subject. The diagnostic method of the invention comprises the use of any of the aforementioned methods for the determination of the likelihood, and/or the aforementioned kits, isolated polynucleotides, nucleic acids probes and primers. Depending on the selected endometriosis-related markers, particularly if used in combination, it is indeed possible according to the present invention to diagnose females having endometriosis with a very high sensibility and a very high specificity.

G) Method for Treating Endometriosis

According to a further aspect, the present invention relates to a method for treating endometriosis. This method comprises the step of modulating the expression level of an endometriosis-related marker selected from the group consisting of:
- i) genes selected from the group consisting of the genes listed in TABLE 1 for which a GENBANK™ gene name is given;
- ii) ribonucleic acids selected from the group consisting of:
  - a) ribonucleic acids giving rise to cDNAs selected from the group consisting of: cDNAs derived from genes defined in i); and cDNAs comprising a sequence selected from SEQ ID NOs: 1 to 16; and
  - b) fragments of the ribonucleic acids defined in a); and
- iii) peptides or proteins encoded by the genes defined in i), or encoded by the ribonucleic acids defined in ii).

In a preferred embodiment, the expression level of at least one of the endometriosis-related markers listed in Table 5 is increased. In another preferred embodiment, the expression level of at least one of the following endometriosis-related markers listed in Table 4 is decreased.

Methods and materials for increasing or decreasing the expression levels of genetic and proteinic markers such as the endometriosis-related markers of the present invention are well known and within the skill of a person in the art. A non-limitative list of known methods and materials includes: diet, vitamins, dietary supplements, gene therapy methods, antisense oligonucleotides, drugs and hormonal medications.

For instance, it is hypothesized that compounds which decrease ROS levels in cells such as ROS scavengers molecules commercialized by METAPHORE PHARMACEUTICALS (www.metaphore.com) not actually used for treating endometriosis could be used according to the methods of treatment of the present invention. Therefore, pharmaceutical compositions for treating endometriosis and comprising substance(s) modulating the expression level of the aforementioned endometriosis-related marker(s) are also within the scope of the present invention.

EXAMPLES

The following examples illustrate the wide range of potential applications of the present invention and are not intended to limit its scope. Modifications and variations can be made therein without departing from the spirit and scope of the invention. Although any methods and materials similar or equivalent to those described herein can be used in the practice for testing the present invention, the preferred methods and materials are described.

Example 1

Genetic markers

1) Problematic

In the absence of any reliable and non-invasive diagnostic tool for the detection of endometriosis, the focus was placed on the identification of genes differentially expressed in the endometrium of female subjects suffering from endometriosis (Endo group) when compared to endometriosis-free subjects (Control group). To achieve this, three quantitative approaches were used, namely differential display, cDNA array hybridization, and specific RT-PCR. Unless specified otherwise, all experiments have been performed using RNA obtained from the enriched glandular fraction of the endometrium. In addition, for some analyses, results were also obtained from RNA isolated from unfractioned endometrial biopsies.

2) Materials and Methods

The following are experimental procedures and materials that were used for the example set forth below.

Patient Recruitment

Common prerequisites for patients to be enrolled in the study carried on for the present example, both in the endometriosis-free control and endometriosis-positive groups, were the following:
premenopausal age;
not currently menstruating;
menstrual cycles between 21 and 35 days;
no acute salpingitis;

no HIV, hepatitis B or C positive diagnosis;
not pregnant or having been pregnant in the last three months;
not currently breastfeeding;
no use of a compound selected from the group consisting of GnRH agonists, Progestins, Danazol, and oral contraceptives in the last three months; and
no use of intra-uterine device (I.U.D.) in the last three months.

Women recruited in the endometriosis-positive group who provided biopsies of the endometrium were selected among women undergoing laparoscopy and for whom the presence of endometriosis was confirmed at the time of surgical examination. Stages of the disease were defined according to the American Society of Reproductive Medicine (ASRM) classification as follows: stage I (minimal), stage II (mild), stage III (moderate), and stage IV (severe).

To be eligible in the control group, women who provided biopsies had to fulfill the following conditions:
undergo laparoscopy for tubal ligation or tubal reanastomosis;
no endometriosis lesion detected in the peritoneal cavity at surgery;
no history of endometriosis in first-degree relatives; and
no infertility indication.

Women with endometriosis (Endo) were subdivided in two experimental groups, namely, EXP 1 (stages I and II) and EXP 2 (stages III and IV).

Experimental groups were further subdivided into proliferative (P) phase and secretory (S) phase groups based on the phase of the menstrual cycle indicated by last menstruations and confirmed by histological examination.

Tissue Samples

Biopsies of the endometrium were obtained from patients under anesthesia prior to laparoscopy with a conventional curette. Harvested tissue was maintained on ice and used for the experiment within four hours.

Experiments were performed either on enriched glandular fractions or on unfractioned biopsies.

Isolation and Preparation of RNA from Enriched Glandular Fraction

Glandular fractions from the endometrium were enriched by enzymatic digestion. The tissue was first cut into small pieces in the presence of HBSS medium (LIFE TECHNOLOGIES™). The pieces were then digested with an enzymatic mixture containing 3.4 mg/ml pancreatin, 0.1 mg/ml hyaluronidase and 1.6 mg/ml collagenase (SIGMA™) for 50 min at 37° C. under 5% $CO_2$. Following enzymatic digestion, glandular cells were separated from the stromal fraction by size exclusion. That is, the digested cell suspension was subjected to successive rounds of filtration through 41 µm and 11 µm filters. The glandular fraction consists of cells that were retained on the filters.

Total RNA was isolated from endometrial glandular cells. The glandular cell fraction was weighed, and cells were resuspended at a final concentration of 100 mg/ml of a denaturing solution containing 2.7 M guanidine thiocyanate, 1.3 M ammonium thiocyanate, and 0.1 M sodium acetate, pH 4.0. The suspension was then extracted twice with phenol/chloroform before precipitation with 1 volume of isopropanol. The RNA pellet was washed with 80% ethanol, and resuspended in $H_2O$ at a final concentration of 1 µg/µl.

Isolation and preparation of RNA from unfractioned biopsies Total cellular RNA was isolated directly from endometrial biopsy tissue.

Briefly, 200-300 mg of biopsy tissue was homogenized using an electric homogenizer in the presence of 3 ml of TRIZOL™ (LIFE TECHNOLOGIES™). RNA was prepared according to the TRIZOL™ manufacturer's protocol. Usually, 2 or 3 additional extractions with phenol/chloroform were necessary to obtain a clear interface. RNA was then precipitated and resuspended as described above.

Differential Display

Differential display (DD) was performed using total RNA isolated from glandular cells or unfractioned biopsies according to Liang and Pardee (*Differential Display: Methods and Protocols*, 1997, Humana Press, Totowa, N.J. p. 1-11). Amplifications were done in a STRATAGENE ROBOCYCLER™ (STRATAGENE™) involving 40 cycles of 94° C. (1 min), 40° C. (2 min), 72° C. (1 min) with a final extension of 7 minutes at 72° C. The following reagents were used: M-MLV Reverse Transcriptase (LIFE TECHNOLOGIES™), $^{33}$P-dATP (AMERSHAM PHARMACIA BIOTECH™, 2500 Ci/mmol), and rTaq DNA Polymerase (AMERSHAM PHARMACIA BIOTECH™).

Cloning of PCR Products

Fragments identified by differential display were cloned using the TA CLONING KIT™ (INVITROGEN™) according to the manufacturer's instructions. Clones containing the desired fragments were identified by colony-PCR as described in Maniatis et al. (Maniatis et al., 1992, *Molecular Cloning: A Laboratory Manual*, Cold Spring Harbor Laboratory Press, Cold Spring Harbor, N.Y.) and using the lacZ-20 and reverse primers.

Reverse-Northern Blot

Colony-PCR products were deposited on positively-charged nylon membranes (BOEHRINGER MANNHEIM™) and hybridized with $^{32}$P-labeled differential display probes. Several clones with the expected differential pattern were selected for sequencing. Clones exhibiting identical sequences were accepted as candidates.

Sequencing

Sequencing was performed using the ABI PRISM RHODAMINE CYCLE SEQUENCING KIT™ (PE APPLIED BIOSYSTEMS™) and run on an automated ABI PRISM 310™ Sequencer (PE APPLIED BIOSYSTEMS™).

cDNA Microarrays

Expression of genes was studied using duplicate membranes of the HUMAN and CANCER ATLAS cDNA ARRAYS™ (CLONTECH LABORATORIES™). Glandular RNA (3 µg) from control individuals and patients at the same phase of the menstrual cycle were reverse transcribed in presence of $\alpha^{32}$P-dATP (AMERSHAM PHARMACIA BIOTECH™, 3000 Ci/mmol). Hybridizations and analyses were performed according to the user's manual provided by the manufacturer.

RT-PCR

Total cellular RNA, previously isolated from glandular cells or unfractioned biopsies as described above, was used as a template for the production of cDNA. Briefly, 1 µg of RNA was digested with 1 U DNAse 1 (LIFE TECHNOLOGIES™ according to the manufacturer's instructions. Digested RNA was then reverse transcribed into cDNA using 200 U M-MLV Reverse Transcriptase in the presence of 0.4 µM random primers (LIFE TECHNOLOGIES™), 2 mM of each of dGTP, dATP, dTTP, and dCTP, and reaction buffer supplied. Following incubation at 37° C. for 1 hour, the reaction was terminated by boiling for 5 minutes. PCR amplification of cDNA was performed according to standard protocols described in Maniatis et al. (Maniatis et al., supra). cDNAs were first normalized by a series of PCR amplifications of the internal control gene, glyceraldehyde phosphate dehydrogenase (GAPDH).

PCR reactions contained 5 µl of cDNA (standardized by GAPDH), 0.5 µM of each of two specific oligonucleotide primers, 0.2 mM of each of dGTP, dATP, dTTP, and dCTP, 1 U rTaq DNA Polymerase, and reaction buffer supplied. Amplifications were performed in a BIOMETRA UNO II™ or T GRADIENT THERMOCYCLER™ (BIOMETRA™) involving 25-40 cycles of 94° C. (45 seconds), a specific annealing temperature (45 seconds), 72° C. (1 min.) with a final extension of 7 minutes at 72° C. Annealing temperatures varied according to the specific oligonucleotide primers used, while the number of cycles varied according to the abundance of the cDNA template in question.

Southern Blot

Southern blots were performed according to standard protocols described in Maniatis et al. (Maniatis et al., Supra). Briefly, following specific PCR amplification of cDNAs described above, samples were separated on 1.5% agarose gels, and transferred onto BIODYNE™ 0.45 µm membranes (PALL CORPORATION™) according to the manufacturer's instructions. The membranes were fixed by UV irradiation, and hybridized overnight at 65° C. with specific plasmid probes which were $^{32}$P-labeled using a random primer labeling kit (MEGAPRIME™ DNA labeling system, AMERSHAM PHARMACIA BIOTECH™). Products were visualized by autoradiography, scanned, and analyzed by MOLECULAR ANALYST™ software (BIO-RAD™). Band intensities were equalized based on the intensity of an internal control (GAPDH).

Sequence Analysis

Nucleotide sequence alignments were performed with GENBANK™ through the BLAST software available at the National Center for Biotechnology Information (NCBI) website (www.ncbi.nih.gov). Given a weak percentage of sequence misreadings in our data and in GENBANK™, homologies of 90% or more were considered as an identity.

Statistical Analysis

Data was analyzed using MICROSOFT EXCEL™. For statistical analysis, the Student-t Test was performed and results were considered significant with a p value of less than or equal to 0.05.

Specificity is defined herein as the probability of absence of a disease marker in the Control group whereas sensitivity is the probability of presence of the disease marker in the Endometriosis group. Calculations for specificity and sensitivity are performed according to the following. First, an arbitrary cut-off value is established on the graphical representation of the sample (RNA, cDNA, protein, or other) in question. For samples that are upregulated in the diseased group, specificity is calculated by counting the number of patients in the Control group that are below the cut-off value, divided by the total number of patients in that group and expressed as a percentage; sensitivity is calculated by counting the number of patients in the Endometriosis group that are above the same cut-off value, divided by the total number of patients in that group and expressed as a percentage. For samples that are downregulated in the disease group, specificity is calculated by counted the number of patients in the Control group that are above the cut-off value, divided by the total number of patients in that group and expressed, as a percentage; sensitivity is calculated by counting the number of patients in the Endometriosis group that are below the same cut-off value, divided by the total number of patients in that group and expressed as a percentage.

3) Results

I—Differential Display (DD)

Enriched glandular cells were isolated from endometrial biopsies and total RNA was extracted. RNA extracts in both the Control and Endo groups were divided into two subgroups according to the phase of the menstrual cycle, namely, proliferative (P) or secretory (S) phase. Initially, differential signals were selected based on their appearance in more than 50% of samples of one group compared to the other. Selected signals were purified from the gel and cloned in E. coli. Several recombinant plasmids for each signal were submitted to the validation step by reverse-Northern blotting as described in the present application. Nucleotide sequence was determined and analyzed for distinct plasmids of each series, and specific primers were synthesized for the next step.

Expression level of the candidates was further analyzed by semi-quantitative RT-PCR on different groups of RNA. Experiments based on cycle number and cDNA amounts were performed to ensure linearity of the PCR reactions. Expression level of GAPDH was used as the internal control to normalize measurements. The Endo group was subdivided in two experimental groups: EXP 1 included minimal and mild stages of the disease (I and II) and EXP 2 consisted of the moderate and severe stages (III and IV) of endometriosis. Table 3 summarizes average values by group for all endometriosis-related markers analyzed.

Cut-off values (not shown) were selected to estimate the clinical value of each marker, namely, specificity and sensitivity. Hence, for each marker, the cut-off value was determined to allow maximal specificity and sensitivity values. Specificity corresponds to the probability of the absence of a marker in the control group and sensitivity represents the probability of the presence of the same marker in the patient group.

A list of all the cDNAs identified by the differential display approach is given herein. For each candidate, the GENBANK™ accession number of homologous genes is given in Table 1. Nucleotide sequence data and corresponding SEQ ID NO are listed in Table 2.

The DD1 marker (SEQ ID NO: 1) shows 94% homology in GENBANK™ with a cDNA cloned from fetal kidney tissue. This cDNA sequence also displays 100% homology to a region in the 22q11 chromosome (AC07064). Expression analysis showed in a significant decrease in the secretory phase of the EXP 1 group compared with the secretory phase of the Control group (p=0.01) (Table 3). With a cut-off established at 0.4, a specificity of 75% and a sensitivity of 90% were obtained (Table 5).

The DD2 marker (SEQ ID NO: 2) corresponds to an expression sequence tag (EST) encoding a phosphoprotein which has also been isolated by differential display from human glioma cells. The homology encompasses an upstream region of 40 bp (97%) and a downstream region of 89 bp (96%). A gap of 40 bp is present in the middle of the alignment between the two sequences. The same alignment was obtained with the I-myc homolog cDNA (HSLMYCH). This may be due to alternate splicing of a common gene in different tissues, or two distinct genes of a given family. Presence of this cDNA has never been described in the endometrium. As shown in Table 3, this gene transcription was downregulated in the Endo group (p=0.04). The cut-off value of 0.13 gives 65% specificity and 77% sensitivity (Table 5).

The DD3 marker (SEQ ID NO: 3) showed a 100% homology with the mitochondrial origin of replication (ori). To date, no mRNA-encoding gene has been mapped in this region of mitochondrial DNA. According to the results obtained for the present example shown in Table 3, expression is markedly decreased in the Endo group (p=0.01). The marker parameters with a 0.7 cut-off value are 63% specificity and 69% sensitivity (Table 5).

The DD4 marker (SEQ ID NO: 4) showed 98% homology with a cDNA isolated from human colon tumors. Up to date, no known function has been associated with this gene. As shown in Table 3, expression is significantly decreased in the secretory phase of the Endo group (p=0.04). With a threshold of 1.3, the candidate gene has a specificity of 83% and a sensitivity of 85% (Table 5).

The DD5 marker (SEQ ID NO: 5) corresponds to a gene having various names such as Cap43, Drg1, TDD-5, rit 42, Ndr 1, Proxy-1 or RTP, the most common and the one used herein being Cap43, Cap43 mRNA has a 1759 bp 3'-untranslated region and its predicted open reading frame encodes a 394 amino acid residue polypeptide. Previous studies have shown a modulated expression of the Cap43 mRNA in various types of cells, but not in endometrial cells nor in endometriosis. As shown in Table 3, a general decrease in the proliferative phase of all the endometriosis patients (p=0.03) was observed. A cut-off value of 1.2 results in 78% specificity and 79% sensitivity (Table 5).

The sequence of the DD6 marker (SEQ ID NO: 6) matches at 97% of homology with a genomic sequence file. In addition, the cDNA segment of DD6 contains an alu sequence at the 3' end. As shown in Table 3, a significant decrease was observed between the Control and EXP 1 in the secretory phase (p=0.018). A cut-off value of 0.4 yields the following parameters: specificity 89%, sensitivity 100% for the EXP 1 (Table 5).

Several ESTs were identical to the sequence DD7 (SEQ ID NO: 7). All known sequences cloned from transformed tissues such as pancreas adenocarcinoma, prostatic intraepithelial neoplasia, or a moderately differentiated endometrial carcinoma. The DD7 cDNA contains also an alu sequence. As shown in Table 3, a severe decrease in gene expression was observed for this marker in the proliferative phase of the Endo group (p=0.019). Specificity of 80% and a sensitivity of 70% with a 0.5 cut-off value were found (Table 5).

Sequence homologies indicated that the sequence of the DD8 marker (SEQ ID NO: 8) was identical to a gene cloned from Jurkat cells, brain, and other tissues. In Table 3, a slight but significant decrease in DD8 expression in the EXP 1 group (p=0.02), with specificity and sensitivity values of 67% and 60% respectively, at a cut off value of 0.6, was observed (Table 5).

The DD9 marker (SEQ ID NO: 9) corresponds to the subunit II of the mitochondrial enzyme, NADH dehydrogenase, which is involved in cellular oxygen metabolism. This gene plays a key role in the electron transport chain and energy production. As seen in Table 3, a substantial increase in the proliferative phase of the Endo group (EXP 1 and EXP 2) is detected (p=0.008). A 0.2 cut-off value provides a specificity of 70% and a sensitivity of 59% (Table 4).

The DD10 marker (SEQ ID NO: 10) corresponds to the NADH dehydrogenase subunit II. As with DD9, this gene product is part of the respiratory enzyme complex localized in the mitochondria. The entire enzyme is composed of 12 different polypeptides. In Table 3, validation of this marker showed a higher level of expression in the proliferative phase of the EXP I group (p=0.04). Diagnostic value of the gene was evaluated with a 0.2 cut-off value giving a specificity of 71% and a sensitivity of 71% (Table 4).

The DD11 marker (SEQ ID NO: 11) corresponds to the cytochrome oxidase (CO3) (described below).

The DD12 marker (SEQ ID NO: 12) corresponds to the transcription factor Forkhead domain protein (FKHR). Its presence in endometrium has never been reported in literature. In Table 3, expression analysis of this marker on unfractioned endometrial tissue RNA showed a decrease of expression in the Endo group (p=0.015). The marker was evaluated with a cut-off value of 23 with a specificity of 81% and sensitivity of 56% when both phases were considered (Table 5). When DD12 expression was analyzed by Northern blotting on unfractioned biopsy RNA samples, a significant decrease in the Endo group was detected compared to the controls (p=0.05) (Table 5). Using a cut-off value of 0.4, the specificity was 55% and the sensitivity was 68%. This result is in agreement with the inventor's initial observation using RT-PCR.

The DD13 marker (SEQ ID NO: 13) corresponds to hUCC1 gene messenger RNA. The same cDNA was previously cloned from colon cancer. In Table 3, expression analysis of this marker with unfractioned tissue RNA showed a higher level of expression in the EXP 2 group (p=0.04). Diagnostic value of the gene was evaluated with a 0.5 cut-off value giving a specificity of 62% and a sensitivity of 64% in the EXP 2 group (Table 4).

The sequence of the DD14 marker (SEQ ID NO: 14) is 98% identical to a recently cloned human cDNA encoding a putative membrane-bound morphoregulatory protein which shows homology with paralemmin, a membrane-bound morphoregulatory protein. As seen in Table 3, an increase in the Endo group (EXP 1 and EXP 2) is detected with unfractioned biopsy RNA (p=0.04). A 1.2 cut-off value provides a specificity of 78% and a sensitivity of 58%, when only the S-phase is considered (Table 4).

The DD15 marker (SEQ ID NO: 15) corresponds to the citrate transport protein, one of the DiGeorge syndrome markers in the 22q11 region. As shown in Table 3, this marker exhibits in unfractioned biopsy RNA a substantial increase of expression in the Endo group (p=$6.10^{-4}$). A specificity of 85% and a sensitivity of 79% were obtained with a cut-off value of 0.18 (Table 4).

The sequence of the DD16 marker (SEQ ID NO: 16) shows 90% homology with some human ESTs and 82% homology with the human mitochondrial 12S rRNA gene. As shown in Table 3, the expression of this marker was down-regulated in the Endo group of unfractioned biopsy RNA (p=$3\times10^{-5}$). With a cut-off value of 2, this marker showed a specificity of 70% and a sensitivity of 78% (Table 5).

II—Other Approaches

In the present example, another semi-quantitative technique, namely reverse-Northern blotting with cDNA arrays, was used to identify other genes that are differentially expressed in endometriosis. The final validation analysis was done by standardized RT-PCR, similar to the differential display approach. Table 1 gives the known GENBANK™ accession number for each gene which were, according to the present invention, identified as an endometriosis-related marker.

Hypoxia-induced factor $1\alpha$ (HIF-$1\alpha$) is one of the two subunits of a transcription factor involved in oxidative stress. As seen in Table 3, statistical analysis showed a significant increase of HIF-$1\alpha$ mRNA in the Endo group (p=0.028). With a cut-off value of 1.1, a specificity of 65% and a sensitivity of 72% were obtained. When HIF-$1\alpha$ expression was analyzed by Northern blotting on unfractioned biopsy RNA samples, a significant increase in the P-phase of the Endo group was detected compared to the control P-phase (p=0.019) (Table 4). Using a cut-off value of 0.95, the specificity was 83% and the sensitivity was 80%. This result is in agreement with the inventors' initial observation on epithelial cells RNA.

The aryl hydrocarbon receptor nuclear translocator (ARNT) (or HIF-$1\beta$) is the second subunit of the hypoxia-induced transcription complex. In fact, ARNT has a dual role: it may be coupled to HIF-$1\alpha$ as in the case of hypoxia, but it may also form a heterodimer with the aromatic (aryl)hydrocarbon receptor (AhR) to counteract toxic situations. In endometriosis, the ARNT gene is transcribed at a higher rate than that observed for its partner, HIF-1α. As seen also in Table 3, a significant increase in the proliferative phase patients of the Endo group (p=0.02) was registered. Specificity of this marker was 67% and sensitivity 83% with a cut-off value of 0.6 (Table 4). These parameters are comparable with the ones for HIF-1α in the proliferative phase. Comparable expression patterns for HIF-1α and ARNT is a strong argument in favor of the oxidative stress pathway (OXPHOS) involvement in endometriosis.

Adenylate kinase is a ubiquitous enzyme that contributes to the homeostasis of the cellular adenine and guanine composition. The adenylate kinase isozyme 3 (AK3) isoform is exclusively located in the inner membrane of mitochondria and its activity is involved in energy transfer. Its modulation has been associated with hypoxia and, more specifically, with HIF1α activity. In Table 3, a severe down-regulation of AK3 expression was observed in the EXP 1 group (p=0.005). The cut-off of 0.75 produced a specificity of 68% and a sensitivity of 82% (Table 5).

The glucose transporter isoform 1 (Glut-1) plays an important role in cellular energy metabolism. As mentioned above, expression of Glut-1 is regulated by the HIF-1α/ARNT transcription factor complex. In addition, Glut-1 expression is induced in various circumstances such as oxidative stress or cellular transformation. In Table 3, a significant up-regulation in Glut-1 expression in the EXP 2 group compared to the Control group (p=0.037) was observed. Moreover, the specificity and sensitivity of Glut-1 are 71% and 67% respectively, when using a cut-off value of 1 (Table 4).

Cellular respiration occurring in the mitochondria results in the production of reactive oxygen species (ROS). Chronic ROS exposure can result in permanent oxidative damage to cellular and mitochondrial proteins, lipids, and nucleic acids. To protect against oxidative damage caused by these toxic products, mammalian cells have evolved protective mechanisms. Detoxifying enzymes include manganese superoxide dismutase (MnSOD), glutathione peroxidase (GPx), catalase (CAT), and glutathione S-transferase (GST). MnSOD is transcriptionnally up-regulated in mitochondria to detoxify superoxide anion ($O_2^-$) by converting it to hydrogen peroxide ($H_2O_2$).

Analysis of MnSOD expression in Table 3 demonstrates a general and significant up-regulation in the entire Endo group compared to Control group (p=0.017). With a cut-off of 0.9, the specificity of MnSOD was 76% and its sensitivity was 58%. Similar results were obtained with unfractioned biopsy RNA, and a significant elevation in the whole Endo group was detected (p=0.003). With a cut-off value of 0.9, the marker exhibited a specificity of 81% and a sensitivity of 53% (Table 4).

As discussed above, GPx is involved in the ROS detoxification pathway in the mitochondria. More specifically, GPx converts the $H_2O_2$ produced by MnSOD into $H_2O$. Statistical analysis showed a significant increase in GPx mRNA expression in the Endo group compared to Controls ($p=1.7\times10^{-1}$), as shown in Table 3. This resulted in a specificity of 100% and sensitivity of 87.5%, when using a cut-off value of 1.2 (Table 4).

In extra-mitochondrial sites, such as peroxisomes, the $H_2O_2$ produced by MnSOD is converted into $H_2O$ by catalase (CAT). Thus CAT functions in ROS detoxification by protecting cells from the $H_2O_2$ that is generated within them. In the present example, a significant decrease in CAT mRNA expression in unfractioned biopsy RNA was observed in the secretory phase of the Endo group compared to Controls (p=0.001), as shown in Table 3. Using a cut-off value of 0.2, the specificity and sensitivity of CAT is 83% and 78%, respectively (Table 5).

The glutathione S-transferase (GST) gene superfamily is one of the major detoxifying and free-radical scavenging systems in mammalian cells. In the present example, a significant diminution in GST expression in the EXP 1 group compared with controls (p=0.026) was observed, as illustrated in Table 5. A direct analysis of Table 3 also shows an increase in GST expression in the EXP 2 group. According to a cut-off value of 0.21, parameters for the EXP 1 group would be a specificity of 54% and a sensitivity of 74% (Table 5).

Endothelial nitric oxide synthase (eNOS) catalyzes the oxidation of L-arginine to nitric oxide (NO) and citrulline. Previous reports have described an up-regulation at the protein level in the endometrium of endometriosis patients during the secretory phase of the cycle (Ota et al., Fertility and Sterility (1998) 69:303-308). In the present example, a significant decrease in eNOS expression when comparing the proliferative phases of the control group and the proliferative phases of the Endo group as a whole (p=0.027) is observed (see Table 3). Using a cut-off value of 0.1, one could define specificity and sensitivity of 77% and 65%, respectively (Table 5).

The so-called Cytochrome oxidase 3 (CO3) gene was published as being up-regulated in hepatocytes by $H_2O_2$ and/or homocysteine. The sequence amplified in the present example corresponded to several cDNAs in GENBANK™ such as the hypoxia-inducible gene 14 which was in fact in the 16S rRNA region of the human mitochondrial genome, and with the TI-227H cDNA, a metastatic marker. Finally, the CO3 gene sequence is entirely homologous to the DD11 sequence (isolated by differential display). The analysis of the CO3 gene expression (and of DD11) revealed a secretory phase-specific diminution, as seen in Table 3, when comparing the Control and Endo groups (p=0.002). When using a cut-off value of 0.58, the specificity and sensitivity of this marker were 83% and 79%, respectively (Table 5).

12S rRNA is one of the two rRNA genes encoded by the mitochondrial genome. In the present example, a significant decrease in 12S rRNA in unfractioned biopsy RNA was observed in the EXP 1 group compared to Controls (p=0.02), as illustrated in Table 3. Using a cut-off value of 1, the specificity and sensitivity of 12S rRNA are 77% and 67%, respectively (Table 5).

TI-227H is a nuclear gene that has homologies with CO3, as described above. As a result of these sequence similarities, the present inventors were interested in determining if the two sequences were, in fact, the same gene, or were perhaps pseudogenes. Interestingly, analysis of TI-227H mRNA expression in unfractioned biopsy RNA, described in the present example, showed different results from those obtained with CO3, suggesting that the two sequences are from different genes. Unlike CO3 expression which decreased in the entire Endo group, expression of TI-227H diminished significantly in the EXP 2 group compared to Controls ($p=2\times10^{-8}$), as shown in Table 3. The specificity and sensitivity of TI-227H are 81% and 100%, respectively, when using a cut-off value of 0.15 (Table 5).

Cytochrome oxidase 2 (CO2) is a mitochondrial-encoded enzyme that participates in the mitochondrial electron-transport chain (ETC) and thus, in the process of oxidative phosphorylation (OXPHOS) which provides essential energy to cells. As shown in Table 3, CO2 mRNA expression in unfractioned biopsy RNA was found to decrease in the proliferative phase of EXP 1 compared to Controls (p=0.02). When using a cut-off value of 0.2, the specificity and sensitivity of CO2 are 64% and 69%, respectively (Table 5). There is experimental evidence reported in the literature showing changes in iron metabolism in response to oxidative stress. One of the key enzymes in this pathway is the mitochondria-located aconitase.

Analysis of the aconitase gene expression (Table 3) showed a decrease in the S-phase of EXP 1 group (p=0.005) and also in the P-phase of EXP 2 (p=0.04). Analysis of mean values of P-phase samples exhibits a decrease of the P-phase of both groups (EXP 1 and EXP 2), but only the latter is significantly lower than the control group. Since the most remarkable decrease is observed in the EXP 1 S-phase, we evaluated the diagnostic power of aconitase on this basis. With a 0.11 cut-off, a specificity of 80% and a sensitivity of 86% were calculated (Table 5).

Encoded by a nuclear gene, adenine nucleotide translocator 1 (ANT-1) is located within the mitochondrial inner membrane. ANT-1 plays an important role in OXPHOS, by exchanging newly-synthesized ATP for spent ADP. To date, modulation of ANT-1 expression in endometrial biopsies has not been reported. In the present example, ANT-1 mRNA expression analyzed by RT-PCR in unfractioned biopsy RNA was found to decrease in the proliferative phase of the Endo group compared to Controls (p=0.007), as shown in Table 3. When using a cut-off value of 1, ANT-1 has a specificity of 86% and a sensitivity of 74% (Table 5). This result was confirmed by Northern-blotting (p=0.016) whereby the specificity and sensitivity values were 75% and 73%, respectively, when a cut-off value of 0.042 was used (Table 5).

ATP synthase, also known as Complex V of the ETC, is encoded by two mitochondrial genes (ATPase 6 and ATPase 8) and 12 nuclear genes. In agreement with its critical role in OXPHOS, mutations in ATP synthase have been associated with mitochondrial diseases. As shown in Table 3, the expression of the β subunit of ATP synthase in unfractioned biopsy RNA increased in the Endo group compared to Controls (p=1×10$^{-3}$). Interestingly, when considering only the proliferative phase of the Endo group, the statistical analysis becomes p=8×10$^{-4}$. When using a cut-off value of 4, the specificity and sensitivity of ATP synthase (β subunit) is 77% and 75%, respectively, when comparing the Endo group and Controls. When analyzing the P-phase of the Endo group, the specificity is 93% and the sensitivity is 64% (Table 4).

B-cell leukaemia/lymphoma-2 (Bcl-2) is a nuclear-encoded anti-apoptotic protein that is localized in the mitochondrial outer membrane. Interestingly, Bcl-2 expression seems to be driven by estradiol in the endometrium throughout the ovarian cycle, whereby high Bcl-2 expression is observed in the proliferative endometrium and is decreased in the secretory phase (Vaskivuo et al (2000) Mol Cell Endocrinol 165: 75-83). Previous studies have analyzed Bcl-2 expression in glandular versus stromal cells, and in eutopic versus ectopic endometrial fractions (Meresman et al. (2000) Fertil. Steril. 74(4): 760-6; Jones et al. (1998) Hum. Reprod. 13(12): 3496-502). In the present study, Bcl-2 expression in unfractioned endometrial biopsy RNA decreased in the Endo group compared to Controls (p=0.01), as shown in Table 3. The specificity and sensitivity of Bcl-2 expression are 54% and 82%, respectively, when using a cut-off value of 4 (Table 5).

Human c-jun proto oncogene (c-jun) is one of the major ubiquitous transcriptional factors which forms the AP1 complex with c-fos. In the present example, c-jun expression was analyzed and a significant up-regulation during the secretory phase of the EXP 1 group (p=0.05) was observed (see Table 3). With a cut-off value of 0.7, the following parameters for the EXP 1 S-phase group were obtained: specificity 75%, sensitivity 67% (Table 4). When tested on unfractioned biopsy RNA, up-regulation of c-jun expression was significant for the Endo group compared to the Control group (p=0.005). With a cut-off value at 1, a specificity of 76% and a sensitivity of 65% were determined (Table 4).

Chicken ovalbumin upstream promoter transcription factor (COUP-TF) is an important regulator of aromatase P450 (P450arom), which is involved in estrogen biosynthesis. In eutopic endometrial stromal cells, binding of COUP-TF to a region upstream of the aromatase promoter mediates the inhibition of aromatase transcription, thus preventing aberrant estrogen production. As shown in Table 3, COUP-TF mRNA expression decreased in the secretory phase of the Endo samples compared to Controls (p=0.01) in unfractioned RNA biopsies. Using a cut-off value of 0.075, the specificity and sensitivity of COUP-TF is 83% and 78%, respectively (Table 5).

Interleukins are involved in the inflammatory process, as encountered in diseases like endometriosis. Transcription analysis of IL-1β in the present example revealed a totally impaired pattern of expression in the Endo group, while the level is rather constant in the control group (see Table 3). In particular, a significant decrease in IL-1β expression was observed in the EXP 2 group (p=0.0002) Based on a scatter graph (not shown) two cut off values were determined, one for a mean value for the Control group and the other for its corresponding standard deviation. Values outside of this range were identified as corresponding to patients with a high likelihood of suffering from endometriosis. A specificity of 78% and a sensitivity of 93% for the Control group mean value of 0.98±0.28 were determined (Table 5).

Connexins are involved in cell interactions and, more specifically, in structures such as gap junctions. Their expression is generally regulated by steroids. Connexin 43 (Cx43) seems to be regulated by estradiol. Generally in the endometrium, connexin 43, as well as some other connexins, show a higher expression by immunohistochemistry at around 11-15 days of the menstrual cycle. They are thought to be specifically involved in implantation, for example during pregnancy. One publication reported an aberrant expression of connexin 43 in all ectopic epithelial tissue samples in endometriotic lesions. No studies have ever measured the level of expression of connexin 43 in eutopic endometrial cells. In the present example, an up-regulation of Cx43 mRNA was observed in the EXP 1 group compared to controls (p=0.048) (Table 3), a difference which was even more significant when only the proliferative phase of the EXP 1 group was considered (p=0.02). With a cut-off value of 1.3, a specificity of 74% and a sensitivity of 48% for the EXP 1 group were obtained (Table 4). By considering the proliferative phase of the EXP 1 group, the marker is more powerful, since the specificity and the sensitivity are 77% and 64%, respectively (Table 4). Heat shock proteins (HSPs) are often induced to protect cells from various stresses. More specifically, heat-shock protein 70 (HSP 70) is induced in response to protein misfolding, DNA damage, metabolic oxidative stress, and hypoxia. It is reported in the present example that the modulation of HSP 70 mRNA in women with endometriosis is sharply elevated in the Endo group compared to the Control group (p=0.01) (see Table 3). As a marker for endometriosis, the specificity and sensitivity of HSP 70 were 73% and 61%, respectively, when using a cut-off value of 0.6 (Table 4). On unfractioned biopsy RNA, a significant increase in the proliferative phase was also detected (p=0.014), the marker thus having a specificity of 71% and a sensitivity of 78% with a cut-off at 0.25 (Table 4).

Heat-shock protein 90 (HSP 90) is part of a protein chaperone system involved in steroid-inducible and exogenous toxin-inducible signaling. In the present example, the analysis of HSP 90 in regard to endometriosis revealed a marked decrease in gene expression when comparing women in the EXP 2 group with Controls ($p=4.3\times10^{-5}$) (see Table 3). When a cut-off value of 0.17 was used in the analysis of the EXP 2 group compared to the control group, the specificity and sensitivity were 75% and 100%, respectively (Table 5).

Phospholipid hydroperoxide glutathione peroxidase 4 (GPx4 or PHGPx) is responsible for reducing hydroperoxides that are produced in peroxidized membranes and oxidized lipoproteins. In unfractioned biopsy RNA, shown in Table 3, GPx4 mRNA expression decreased in the secretory phase of the EXP I group compared to Controls ($p=5\times10^{-3}$). Using a cut-off of 0.1, the specificity of GPx4 is 83% and the sensitivity is 75% (Table 5).

Glucose-regulated protein 78 (GRP 78) is a stress-response protein related to HSP70 that is induced by agents or conditions that adversely affect the function of the endoplasmic reticulum, such as homocysteine. In the present example, expression of GRP 78 in unfractioned biopsy RNA decreased in the secretory phase of the Endo group compared to Controls ($p=6\times10^{-3}$), as shown in Table 3. The specificity and sensitivity of GRP 78 are 92% and 78%, respectively, when using a cut-off value of 3.

Cyclooxygenase-2 (cox2), also called prostaglandin synthase-2 (PG-2), is involved in prostaglandin synthesis. Its possible involvement in endometriosis has been discussed in relation to increased aromatase activity in ectopic lesions but, to date, there is no evidence of cox2 dysregulation in eutopic endometrial cells. In unfractioned biopsy RNA, shown in Table 3, cox2 mRNA expression significantly increased in the EXP 1 group compared to Controls ($p=0.01$). Using a cut-off value of 6, the specificity of COX2 is 69% and the sensitivity is 62% (Table 4).

III—Combination of Markers

Having found many genetic markers differentially expressed in Control and Endo groups, the inventors tested the hypothesis that differentially expressed genes used in combination might provide a more powerful diagnostic tool than evaluation of single genes. This is especially true given the high level of genetic heterogeneity between individuals.

Table 11 show examples of combination of genetic markers. Specificity and sensitivity were calculated as described above (see statistical analysis). Briefly, specificity indicates the absence of a marker in the control group and sensitivity indicates the presence of a marker in the ENDO group. All 3 genetic markers of interest were tested on the same individual patient samples, thus allowing combinations to be made. For each patient sample, the presence of a given marker was assigned a score of 1, while the absence of the same marker was assigned a score of 0 (the presence and absence of a marker are defined according to being above or below the assigned cut-off value). Following the application of this algorithm to all 3 genes of interest, the marker scores were combined and converted to percentages according to the following: for combinations of 2 markers, 0% represents a score of 0 for both markers, 50% represents a score of 0 for 1 marker and a score of 1 for the other marker, and 100% represents a score of 1 for both markers; for combinations of 3 markers, 0% represents a score of 0 for all 3 markers, 33% represents a score of 1 for 1/3 markers, 67% represents a score of 1 for 2/3 markers, and 100% represents a score of 1 for all 3 markers. These percentages were then graphed, and new specificity and sensitivity values were calculated—these values are indicated in Table 11.

An example of the power of combinations of markers is shown in Table 11, whereby a combination of two markers increased the sensitivity of the diagnosis up to 100%. A combination of three markers increased both specificity and sensitivity. Other combinations of numerous markers would also yield improved specificity and sensitivity, thereby ameliorating the methods and kit according to the present invention.

4) Conclusion

The results presented herein show that the genetic makers listed in Table 1 are all excellent endometriosis markers. The use of differentially expressed genes therefore represents an alternative means to identify diseased individuals and grade endometriosis. By combining two, three and more of these markers, it is also possible to increase the specificity and the sensitivity of the diagnosis.

Many of the genes among the markers of the present invention are associated with mitochondria. Five among the sixteen DD markers were in this category. This observation led the inventors to further investigate in this field. Indeed, physiologically a number of key metabolic reactions, such as oxidative phosphorylation (OXPHOS) imply the mitochondria. Hence, as shown in Table 3, modulation of 22 OXPHOS- and/or mitochondria-related genes, such as HIF-1α, ARNT or NADH dehydrogenase, was observed in the endometrial tissue of endometriosis patients. This strongly suggests that the OXPHOS pathway is involved in endometriosis and that it is possible to determine the likelihood of endometriosis in a female subject by assaying endometrial cells sample for the expression level of at least one endometriosis-related marker involved in the oxidative phosphorylation pathway and/or the internal redox potential sensors pathway (OXPHOS) of said endometrial cells.

Interestingly, three differentially expressed cDNAs containing alu sequences were isolated and identified as endometriosis-related markers. Similarly, another heterogeneous group of endometriosis-related markers were cellular stress markers (heat shock proteins, CAP43, Connexin 43, RNA helicase). It is therefore tempting to speculate that most genes containing an alu sequence and/or cellular stress markers could be used as endometriosis-related markers according to the present invention.

Example 2

Proteinic Markers

1) Problematic

Having found many genetic markers differentially expressed in Control and Endo groups of women, the inventors tested the hypothesis that protein measurement of protein product(s) derived from these genetic markers could also be a suitable approach for the diagnosis of endometriosis.

Since the marker DD5 (namely Cap43) was deregulated at the mRNA level in the endometrium of women suffering from endometriosis, the present inventors have characterized the expression of the protein encoded by the same gene. This was performed by Western blotting.

Cap43 mRNA has a 1759 bp 3'-untranslated region and its predicted open reading frame encodes a 394 amino acid residue polyprotein with a deduced molecular weight of 43,400 Dalton and an isoelectric point of 5.3. Previous studies have shown a modulated expression of the Cap43 gene's mRNA in various types of cells. However, the Cap43 protein has never been used as a marker in any disease, including endometriosis. In the present example, protein extracts isolated from endometrial tissue biopsies from control and diseased populations were screened for Cap43 protein expression and the results presented herein show that this protein is a suitable marker for endometriosis 2) Materials and Methods Patient Recruitment and Tissue Samples Tissue biopsies from control and endometriosis-positive populations were obtained as described previously in Example 1 herein.

Isolation and Preparation of Proteins from Unfractioned Biopsies

Total cellular protein extracts were isolated directly from tissue biopsies. Briefly, 200-300 mg of biopsy tissue was homogenized using an electric homogenizer in the presence of 3 ml of lysis buffer (20 mM Tris-HCl pH 7.5 containing 0.1 M NaCl, 2% SDS, 5 mM EDTA and 0.5 µg/ml leupeptin, 2 µg/ml aprotinin and 200 µg/ml PMSF) at room temperature, lysed 10 min at 100° C. and centrifuged 20 min at 14000 g. Protein determination of supernatants was made using the DC protein assay (BIO-RAD™) according to the supplier's instructions. Samples were diluted in 20 mM Tris-HCl pH 7.5 and dotted onto nitrocellulose membranes (2.5 and 5 µg) using a 96-wells GIBCO-BRL™ dotter device. The membranes were blocked overnight in 2.5% dry milk powder in TST buffer (10 mM tris-HCl pH 7.5 containing 100 mM NaCl and 0.1% TWEEN-20™), incubated in a dilution of either 1:2000 of primary antiserum anti-CAP 43 (SKULDTECH™, Universite Montpelier II, France) or anti-actin (SANTA CRUZ BIOTECHNOLOGY™) for one hour, washed twice for 5 min with TST and incubated for another hour with an horseradish-peroxidase (HRP)-conjugated goat anti-rabbit immunoglobulin-specific polyclonal antibody (1:2000 dilution in 5% milk-TST), washed 3 times 10 min with TST and visualized by ECL reagent according to the supplier's protocol (AMERSHAM PHARMACIA BIOTECH™). Levels of Cap43 relative to actin were measured by scanning the autoradiograms and densitometry of dots was performed using the program MOLECULAR ANALYST™.

3) Results

Using anti-CAP 43 polyclonal antibodies, the present inventors screened protein extracts isolated from endometrial tissue biopsies from control and diseased populations. As shown in Table 3, two types of experiments were performed. In the first experiment, all proliferative and secretory control and experimental groups were included in order to compare the presence of Cap43 in both phases of the ovarian cycle. In the second experiment, only secretory phase groups were tested, and in this way, the number of samples analyzed could be increased.

Results from the first experiment show that the Cap43 protein was expressed in higher levels in the secretory phase of the ovarian cycle, with a mean upregulation in the control group of more than two fold in the secretory phase compared to the proliferative phase (1.92±0.21 CTL S vs. 0.55±0.06 CTL P). In addition, by comparing the control and Endo groups, it appears that there is a significant decrease in Cap43 in the secretory phase of the Endo group (p=0.05), with specificity and sensitivity values of 71% and 57%, respectively, when a cut-off of 1.35 is used (Table 5).

In the second experiment in which only samples in the secretory phase were analyzed, there is also a significant decrease in the secretory phase of the Endo group (p=0.001). Using a cut-off of 1.1, the specificity is 77% and the sensitivity is 61% (Table 5).

4) Conclusion

These results confirm that, like the Cap43 mRNA, the Cap43 protein is differentially expressed in the endometrial cells of endometriosis-free compared to women having endometriosis. It is therefore justified to believe that it is the same for all the endometriosis-related genetic markers listed in Table 1.

The use of differentially expressed genes or their derived protein products (such as translated proteins or peptides) therefore represents an alternative means for determining the likelihood of endometriosis in females and for grading this disease in female suffering from it.

TABLE 1

Endometriosis-related markers

| Applicant Reference | | | GENBANK ™ Reference | | | |
|---|---|---|---|---|---|---|
| SEQ ID NO | Arbitrary name | GENBANK ™ gene name | Accession No | Type | No of bases | Date |
| 1 | DD1 | — | AL050039; AC007064 | EST; EST | 6241 124823 | 18-Feb-00 27-May-00 |
| 2 | DD2 | — | AF084555 | EST | 5171 | 1-Sep-99 |
| 3 | DD3 | — | J01415 | DNA | 16569 | 18-Apr-00 |
| 4 | DD4 | — | AA829538 | EST | 1329 | 29-Apr-98 |
| 5 | DD5 | Nickel-specific induction protein (CAP43) | AF004162 | mRNA | 2972 | 24-Jan-00 |
| 6 | DD6 | — | AL034374 | EST | 101270 | 29-Apr-00 |
| 7 | DD7 | — | AI567884; AA558871; AI890794 | EST; EST; EST | 500 487 2501 | 14-May-99 9-Sep-97 7-Mar-00 |
| 8 | DD8 | RNA helicase | AB028449 | mRNA | 7037 | 18-Feb-00 |
| 9 | DD9 | NADH dehydrogenase | AF004342 J01415 | DNA DNA | 320 16569 | 19-Jul-97 18-Apr-00 |
| 10 | DD10 | NADH dehydrogenase | AF014897 J01415 | DNA DNA | 1041 16569 | 6-May-99 18-Apr-00 |
| 11 | DD11 | Cytochrome Oxidase 3 (CO3) | AB017708 | DNA | 346 | 26-Sep-98 |
| 12 | DD12 | transcription factor Forkhead domain protein (FKHR) | AF032885 | mRNA | 5723 | 19-Feb-98 |
| 13 | DD13 | hUCC1 | AJ250475 | mRNA | 2073 | 1-Jul-00 |
| 14 | DD14 | Paralemmin | AK000278 | mRNA | 2197 | 22-Feb-00 |
| 15 | DD15 | Citrate transport protein | X96924 | DNA | 2270 | 9-Oct-97 |
| 16 | DD16 | — | AC022148 | DNA | 198751 | 26-Aug-00 |
| | | 12S mitochondrial RNA (12S rRNA) | J01415 | DNA | 16569 | 18-Apr-00 |
| | | Hypoxia-induced factor 1α (HIF1α) | NM_001530 | mRNA | 3933 | 31-Oct-00 |
| | | Aryl hydrocarbon Receptor Nuclear Translocator (ARNT) | NM_001668 | mRNA | 2616 | 31-Oct-00 |
| | | Adenylate Kinase isozyme 3 (AK3) | X60673 | mRNA | 1707 | 18-Jan-95 |
| | | Glucose Transporter isoform 1 (Glut-1) | aa368897 | mRNA | 288 | 21-Apr-97 |

TABLE 1-continued

Endometriosis-related markers

| SEQ ID NO | Applicant Reference Arbitrary name | GENBANK™ gene name | GENBANK™ Reference Accession No | Type | No of bases | Date |
|---|---|---|---|---|---|---|
| | | Manganese SuperOxide Dismutase (MnSOD) | X14322 | mRNA | 977 | 12-Nov-90 |
| | | Glutathione Peroxidase (GPx) | X13709 | mRNA | 819 | 6-Apr-95 |
| | | Catalase (CAT) | NM_001752 | mRNA | 2279 | 31-Oct-00 |
| | | Glutathione S-transferase (GST) | X15480 | mRNA | 725 | 12-Sep-93 |
| | | Endothelial nitric oxide synthase (eNOS) | M93718 | mRNA | 4077 | 27-Apr-93 |
| | | TI227H | DD50525 | mRNA | 3911 | 10-Feb-99 |
| | | Cytochrome Oxidase 2 (CO2) | J01415 | DNA | 16569 | 18-Apr-00 |
| | | aconitase | NM_001098 | mRNA | 2467 | 31-Oct-00 |
| | | Adenine Nucleotide Translocator 1 (ANT-1) | NM_001151 | mRNA | 1320 | 31-Oct-00 |
| | | ATP synthase | X03559 | mRNA | 1807 | 30-Dec-97 |
| | | B-cell leukaemia/lymphoma-2 (Bcl-2) | NM_000633 | mRNA | 6030 | 3-Feb-01 |
| | | Human c-jun proto oncogene (c-jun) | J04111 | DNA | 3622 | 6-Jan-95 |
| | | Chicken Ovalbumin Upstream Promoter Transcription Factor (COUP-TF) | X16155 | mRNA | 1513 | 19-Jul-95 |
| | | Interleukin 1β (IL-1β) | m15330 | mRNA | 1497 | 6-Jan-95 |
| | | Connexin 43 (Cx43) | m65188 | mRNA | 1314 | 1-Nov-94 |
| | | Heat-Shock Protein 70 (HSP 70) | m11717 | DNA | 2691 | 8-Nov-94 |
| | | Heat-Shock Protein 90 (HSP 90) | x15183 | mRNA | 2912 | 30-Jan-95 |
| | | Phospholipid hydroperoxide glutathione peroxidase 4 (GPx4) | NM_002085 | mRNA | 896 | 31-Oct-00 |
| | | Glucose-regulated protein 78 (GRP78) | m19645 | DNA | 5470 | 8-Nov-94 |
| | | Cyclooxygenase-2 (cox2) | m90100 | mRNA | 3387 | 31-Dec-94 |

TABLE 2

Nucleotide sequences of endometriosis-related markers identified by differential display

| SEQ ID NO | Arbitrary Name | Nucleotide Sequence |
|---|---|---|
| 1 | DD1 | ggttagtaattctgcagatcgctagctcgacgattcattggctgaatagccagtggtgcaggacatatgc acagtgtctgacctcagtaacttcactctcatacatatgtattaggacaccaacacatgtgtgcatataa gatgtatgatagatattgcaacaagtaataatttactgtcctatttataggattttaaacttaaactactttca ccctatttccaaaaaaa |
| 2 | DD2 | gactgtactgaaagggccaagagtaaatgccttcgttttgttttttcgtttnttttgttttagcttttgttaaaac gtctatagattggcagttaatgctgaatttgtcaaatacccctccaaaattatactttgtatttaaaaaata aatgggatctacctaatttccaa |
| 3 | DD3 | cgactgtatgntgaacgtaggtgcgataaataataggatcgaggcaggaatcaaagacagatactg cgacataggqtgctccggctccagcgtctcgcaatgctatcgcgtgcataccccaa |
| 4 | DD4 | cgactgtggacgagagggaacctggtggtgggaccatggaggcagggtgcagaggtgcacaata aaaattgattatcatcgttttgagaatgttgttggttcccccca |
| 5 | DD5 | aagctttggtcagagtgaattgaatattgtaagtcagccactgggacccgaggattctgggaccccgc agttggaggaggaatnagtccagccttccaggtggcgtgagaggcaatgactcgttacctgccgcc catcaccttggaggccttccctggccttgagtagaaagtcggggatcggggcaagagaggctgagt acggatgggaaactattgtgcacaagtcttttccanaggagtttcttaatgagagtttgtatttatttccaga ccaataaatttgtaactttgcaa |
| 6 | DD6 | aagctttggtcagggatagagaatgaaagtgagatcatttagatcttagaaaggnagatgttnggctn gggcacggtggctcacacctgtaatcccagcacttgggaagccatggtgggcagatcatttgagctca ggagtttgcaaccagcctgggcaatatggcaagaccccatctgtacaa |
| 7 | DD7 | ttgtatttttagtaaagacggggttcactatgttggccaggctggtctcgaactcctgacctcgtgatcca cccaccttggcctcccaatcttatttgctttacaagtcctgcttcagggttaccttccctgaccaaagctt |
| 8 | DD8 | tctaatgcataataaaatgaaaggaatcgtaaaacagtttcgttccaaaaagtcagagataaagacta tccatgaaggttcacttttgaggcaagaacccttttttatgcaagactatgtggcatcagaaaactaaat gtgattcaccaacatgccagccaatgttcattaaaaaatctgtcccttactaacaggtgcaacagcgacc gggaacatcaccttacacagtataacgtggaaagaaaagacaacattgggngcacttctcntctcca aaaccttatctttcnattcagctttancatntactgcaggactg |
| 9 | DD9 | ttgattcggttcagtctaatcctttttgtatcactcataggccagacttnagggctaggatgatgattaataa gagggatgacataactattagtggcaggtagttgtttgtagggctcatggtaggggtaaaaggagggc |

TABLE 2-continued

Nucleotide sequences of endometriosis-related markers
identified by differential display

| SEQ ID NO | Arbitrary Name | Nucleotide Sequence |
|---|---|---|
| | | aatttctagatcaaataataagaaggtaatagctactaagaagaattttatggagaaagggacgcgg<br>gcggggatatagggtcgaagccgcactcgtaaggggtggattttctatgtagccgttgaagaagctt |
| 10 | DD10 | gtaggcagttgaggtggattaaaccaaacccagctacgcaaaatcctnagcatactcctcaattaccc<br>acataggatgaataatagcagttctaccgtacaaccctaacataacctgcttaatttaactatttatattat<br>cctaactactaccgcattcctactactcaacttaaactccagcaccacgaccctactactatctcgcacc<br>tgtaacaagctaacatgactaacacccttaattccatccaccctcctctccctaggaggcctgaccccg<br>ctaancgngcttttttgcccaattgggcattancgagattca |
| 11 | DD11 | gtaggcctaaaagcagccaccaattaagaaagcgttcaagctcaacacccactacctnaaaaaatc<br>ccaaacatataactgaactcctcacacccaattgngaccaatctatcaccctatagaagaactaatgtt<br>agtataagtaacatgaaaacattctcctccgcataagccttgcgtcagattaaaacactgaactgaca<br>attaacagcccaatatctacaatcaaccaacaagtcattattaccctcactgtcaacccaacacaggc<br>atgctcataaggaaaggttaaaaaaagtaaaaggaactcggcaaatcttaccncgc |
| 12 | DD12 | gactgtgacatggaatccatcattcggaatgacctcatggatggagatacattggattttaactttgaca<br>atgtgttgcccaaccaaagcttcccacacagtgtcaagacaacgacacatagctgggtgtcaggctg<br>agggttagtgagcaggttacacttaaaagtacttcagattgtctgacagcaggaactgagagaagca<br>gtccaaagatgtctttcaccaactcccttttagttttcttggttaaaaaa |
| 13 | DD13 | ggttgagtttgtccattgctagggagagacttccagtaataaaatttactattctagatgcttctactgttatg<br>ttttatctacccatttatctttcttagttaccaggagaaatgtgtgacacctatattataatgaaaacaatctta<br>ttacttatagtttatctatattaaacaaatttaattgcatttaaagcattctttgatattgttgcttttgcaataaat<br>atggataatcttggttataagggagttaaaacaatgctgtaataaaaaagtgtttcatgtgatcaaa |
| 14 | DD14 | ttcatcatcttctttttcctcatnnatctccttccttaacctagaaggtatgtaggactttggaaggtcaggga<br>tattagcatagatgtcctcaattgactcttctgctcttcttctctttccactttcacagatcttataatgtcttctgt<br>tgtccgctcaattgactttagtttctttaaaatggcctcttccttcgttgagaagcttaagccga |
| 15 | DD15 | ggcctggcttcaccgcattccaggctgcagcccctgcttctcccgccattgccttaactgccctcgggc<br>cctctctccgccccggacagggtggcaccaccactctcaggaccaccctgccaaggcagaataaa<br>ccggatcctgttgc |
| 16 | DP16 | aagcttgcaccatgacctaacgttttatgtaaatacttgtgtttagtacctttaaggttttgcagaagatgg<br>cggtgtataggctgaattagcaagagatagtgaggtttactggggtttattgattcaaa |

TABLE 3

Summary of average values (±SEM, standard error of the mean) by group for the endometriosis-related markers

| Name | CTL P▣ | CTL▫ | CTL | EXP I P | EXP I S | EXP I |
|---|---|---|---|---|---|---|
| DD1 (epith) | 0.24 ± 0.04 | 0.81* ± 0.20 | 0.55 ± 0.12 | 0.60 ± 0.21 | 0.15* ± 0.03 | 0.38 ± 0.12 |
| DD2 (epith) | 1.21 ± 0.62 | 0.42 ± 0.14 | 0.76* ± 0.29 | 0.10 ± 0.04 | 0.09 ± 0.03 | 0.10 ± 0.02 |
| DD3 (epith) | 0.98 ± 0.09 | 0.64 ± 0.03 | 0.88* ± 0.07 | 0.79 ± 0.09 | 0.57 ± 0.04 | 0.68 ± 0.05 |
| DD4 (epith) | 0.87 ± 0.18 | 1.29* ± 0.23 | 1.00 ± 0.15 | 0.77 ± 0.12 | 0.79 ± 0.14 | 0.78 ± 0.09 |
| DD5 (epith) | 1.92* ± 0.38 | 3.65 ± 1.85 | 2.86 ± 1.02 | 0.85 ± 0.25 | 1.61 ± 0.50 | 1.19 ± 0.27 |
| DD5 | n.a. | 1.81* ± 0.17 | n.a. | n.a. | 1.08 ± 0.11 | n.a. |
| (biop PROT+) (2 experiments) | 0.55 ± 0.06 | 1.92* ± 0.21 | 1.28 ± 0.18 | 0.62 ± 0.07 | 1.45 ± 0.13 | 1.05 ± 0.11 |
| DD6 (epith) | 2.18 ± 1.32 | 0.83* ± 0.23 | 1.42 ± 0.59 | 0.49 ± 0.12 | 0.15* ± 0.03 | 0.32 ± 0.08 |
| DD7 (epith) | 1.49* ± 0.39 | 2.47 ± 1.37 | 2.02 ± 0.76 | 0.38 ± 0.12 | 0.35 ± 0.09 | 0.37 ± 0.08 |
| DD8 (epith) | 0.81 ± 0.14 | 1.01 ± 0.20 | 0.88* ± 0.11 | 0.59 ± 0.10 | 0.52 ± 0.12 | 0.56* ± 0.08 |
| DD9 (epith) | 0.14* ± 0.03 | 0.41 ± 0.14 | 0.29 ± 0.08 | 0.29 ± 0.06 | 0.44 ± 0.22 | 0.36 ± 0.10 |
| DD10 (epith) | 0.17* ± 0.03 | 0.23 ± 0.02 | 0.19 ± 0.02 | 0.27* ± 0.04 | 0.13 ± 0.02 | 0.20 ± 0.03 |
| DD11 (biop) | | See CO3 | | | | |
| DD12 (biop) | 27.92 ± 5.01 | 40.20 ± 5.46 | 34.73* ± 3.97 | 14.48 ± 2.29 | 35.42 ± 3.85 | 26.11 ± 3.42 |
| DD12 (biop NB) | 0.47 ± 0.14 | 1.15 ± 0.26 | 0.78* ± 0.15 | 0.46 ± 0.15 | 0.52 ± 0.15 | 0.49 ± 0.10 |
| DD13 (biop) | 0.72 ± 0.13 | 0.24 ± 0.08 | 0.45* ± 0.09 | 0.83 ± 0.17 | 0.24 ± 0.06 | 0.48 ± 0.10 |
| DD14 (biop) | 1.36 ± 0.25 | 0.77 ± 0.14 | 1.03* ± 0.15 | 2.65 ± 0.83 | 1.23 ± 0.19 | 1.86 ± 0.41 |
| DD15 (biop) | 0.12 ± 0.07 | 0.10 ± 0.06 | 0.11* ± 0.05 | 0.49 ± 0.12 | 0.32 ± 0.08 | 0.43 ± 0.08 |
| DD16 (biop) | 2.54 ± 0.35 | 2.46 ± 0.32 | 2.50* ± 0.23 | 0.63 ± 0.16 | 1.49 ± 0.11 | 0.98 ± 0.15 |
| HIF1α (epith) | 0.84 ± 0.10 | 1.34 ± 0.15 | 0.99* ± 0.10 | 1.29 ± 0.13 | 1.23 ± 0.16 | 1.26 ± 0.10 |
| HIF1α (biop NB) | 0.78* ± 0.08 | 1.82 ± 0.35 | 1.20 ± 0.18 | 1.06 ± 0.14 | 1.82 ± 0.32 | 1.35 ± 0.18 |
| ARNT (epith) | 0.53* ± 0.11 | 1.38 ± 0.65 | 1.00 ± 0.37 | 1.04 ± 0.19 | 1.76 ± 0.61 | 1.37 ± 0.30 |
| AK3 (epith) | 0.60 ± 0.17 | 1.62 ± 0.32 | 1.14* ± 0.22 | 0.22 ± 0.07 | 0.62 ± 0.18 | 0.41* ± 0.10 |
| Glut-1 (epith) | 0.51 ± 0.12 | 0.86 ± 0.18 | 0.69* ± 0.11 | 0.63 ± 0.21 | 1.28 ± 0.65 | 0.81 ± 0.29 |
| MnSOD (epith) | 0.62 ± 0.04 | 0.96 ± 0.23 | 0.84* ± 0.15 | 0.10 ± 0.23 | 3.89 ± 2.32 | 2.62 ± 1.32 |
| MnSOD (biop) | 0.68 ± 0.06 | 0.89 ± 0.16 | 0.76* ± 0.08 | 0.92 ± 0.18 | 2.20 ± 0.41 | 1.56 ± 0.26 |

TABLE 3-continued

Summary of average values (±SEM, standard error of the mean) by group for the endometriosis-related markers

| | | | | | | |
|---|---|---|---|---|---|---|
| GPx (epith) | 0.34 ± 0.08 | 0.80 ± 0.11 | 0.49* ± 0.08 | 1.50 ± 0.18 | 2.01 ± 0.19 | 1.75 ± 0.14 |
| catalase (biop) | 0.60 ± 0.08 | 0.49* ± 0.08 | 0.55 ± 0.06 | 0.88 ± 0.25 | 0.13 ± 0.04 | 0.59 ± 0.17 |
| GST (epith) | 0.40 ± 0.09 | 0.38 ± 0.12 | 0.39* ± 0.07 | 0.21 ± 0.08 | 0.15 ± 0.03 | 0.19* ± 0.05 |
| eNOS (epith) | 0.35* ± 0.08 | 0.39 ± 0.20 | 0.36 ± 0.08 | 0.17 ± 0.05 | 0.40 ± 0.09 | 0.27 ± 0.05 |
| CO3/DD11 (epith) | 0.44 ± 0.09 | 0.77* ± 0.11 | 0.55 ± 0.08 | 0.51 ± 0.08 | 0.31 ± 0.07 | 0.41 ± 0.06 |
| 12S rRNA (biop) | 4.12 ± 1.02 | 3.02 ± 0.70 | 3.61* ± 0.63 | 0.78 ± 0.42 | 2.82 ± 1.19 | 1.56* ± 0.55 |
| TI227H (biop) | 0.33 ± 0.04 | 0.30 ± 0.06 | 0.32* ± 0.04 | 0.43 ± 0.12 | 0.45 ± 0.18 | 0.44 ± 0.10 |
| CO2 (biop) | 0.58* ± 0.16 | 0.37 ± 0.15 | 0.48 ± 0.11 | 0.16* ± 0.04 | 0.40 ± 0.05 | 0.25 ± 0.04 |
| aconitase (biop) | 0.43 ± 0.10 | 0.18* ± 0.02 | 0.31 ± 0.06 | 0.30 ± 0.07 | 0.07* ± 0.02 | 0.21 ± 0.05 |
| ANT-1 (biop) | 0.02* ± 0.003 | 0.03 ± 0.01 | 0.03 ± 0.004 | 0.01 ± 0.001 | 0.08 ± 0.02 | 0.03 ± 0.01 |
| ANT-1 (biop NB) | 0.09* ± 0.02 | 0.02 ± 0.01 | 0.06 ± 0.01 | 0.05 ± 0.02 | 0.02 ± 0.01 | 0.04 ± 0.01 |
| ATP synthase (biop) | 2.28 ± 0.32 | 5.28 ± 1.53 | 3.67* ± 0.77 | 5.06 ± 1.05 | 9.43 ± 1.43 | 6.72 ± 0.95 |
| | 2.28* ± 0.32 | 5.28 ± 1.53 | 3.67 ± 0.77 | 5.06 ± 1.05 | 9.43 ± 1.43 | 6.72 ± 0.95 |
| Bcl-2 (biop) | 4.61 ± 1.13 | 6.11 ± 1.64 | 5.30* ± 0.97 | 3.96 ± 0.90 | 0.82 ± 0.31 | 2.76 ± 0.65 |
| c-jun (epith) | 0.51 ± 0.09 | 0.51* ± 0.08 | 0.51 ± 0.07 | 0.53 ± 0.10 | 0.85* ± 0.11 | 0.66 ± 0.08 |
| c-jun (biop) | 0.68 ± 0.11 | 1.02 ± 0.18 | 0.82* ± 0.11 | 0.98 ± 0.26 | 1.84 ± 0.40 | 1.38 ± 0.25 |
| COUP-TF (biop) | 0.05 ± 0.01 | 0.22* ± 0.05 | 0.13 ± 0.03 | 0.08 ± 0.04 | 0.06 ± 0.03 | 0.07 ± 0.02 |
| IL-1β (epith) | 1.02 ± 0.09 | 0.86 ± 0.10 | 0.98* ± 0.07 | 1.31 ± 0.36 | 1.14 ± 0.28 | 1.23 ± 0.23 |
| Cx43 (epith) | 1.06 ± 0.15 | 0.72 ± 0.32 | 0.95* ± 0.14 | 1.69 ± 0.21 | 1.06 ± 0.19 | 1.39* ± 0.16 |
| | 1.06* ± 0.15 | 0.72 ± 0.32 | 0.95 ± 0.14 | 1.69* ± 0.21 | 1.06 ± 0.19 | 1.39 ± 0.16 |
| HSP 70 (epith) | 0.56 ± 0.09 | 0.30 ± 0.07 | 0.42* ± 0.06 | 1.04 ± 0.28 | 0.91 ± 0.26 | 0.98 ± 0.19 |
| HSP 70 (biop) | 0.26* ± 0.13 | 1.38 ± 0.44 | 0.86 ± 0.28 | 0.80 ± 0.20 | 0.80 ± 0.31 | 0.80 ± 0.18 |
| HSP 90 (epith) | 0.38 ± 0.08 | 0.32 ± 0.06 | 0.36* ± 0.06 | 0.37 ± 0.06 | 0.19 ± 0.03 | 0.28 ± 0.04 |
| GPx4 (biop) | 0.07 ± 0.01 | 0.21* ± 0.04 | 0.13 ± 0.02 | 0.06 ± 0.02 | 0.07* ± 0.02 | 0.07 ± 0.01 |
| GRP78 (biop) | 4.76 ± 0.57 | 7.97* ± 1.75 | 6.24 ± 0.90 | 6.49 ± 1.38 | 1.63 ± 0.71 | 4.64 ± 1.03 |
| cox2 (biop) | 3.04 ± 0.98 | 5.88 ± 2.10 | 4.35* ± 1.12 | 9.28 ± 1.97 | 9.73 ± 2.91 | 9.46* ± 1.60 |

| Name | EXP II P | EXP II S | EXP II | ENDO P | ENDO S | ENDO |
|---|---|---|---|---|---|---|
| DD1 (epith) | 2.77 ± 1.96 | 1.39 ± 1.02 | 1.94 ± 0.97 | 1.36 ± 0.72 | 0.74 ± 0.49 | 1.03 ± 0.42 |
| DD2 (epith) | 0.09 ± 0.02 | 0.28 ± 0.13 | 0.21 ± 0.08 | 0.10 ± 0.03 | 0.18 ± 0.06 | 0.14* ± 0.03 |
| DD3 (epith) | 0.41 ± 0.10 | 0.60 n.a. | 0.45 ± 0.08 | 0.71 ± 0.08 | 0.58 ± 0.04 | 0.65* ± 0.05 |
| DD4 (epith) | 0.80 ± 0.36 | 0.36 n.a. | 0.69 ± 0.28 | 0.78 ± 0.11 | 0.75* ± 0.13 | 0.77 ± 0.08 |
| DD5 (epith) | 1.11 ± 0.62 | 28.06 ± 23.75 | 17.70 ± 14.73 | 0.92* ± 0.24 | 13.37 ± 10.65 | 7.32 ± 5.51 |
| DD5 (biop PROT+) | n.a. | 1.34 ± 0.29 | n.a. | n.a. | 1.12* ± 0.10 | n.a. |
| (2 experiments) | n.a. | 0.93 ± n.a. | n.a. | n.a. | 1.41* ± 0.12 | 1.04 ± 0.11 |
| DD6 (epith) | 1.06 ± 0.72 | 0.54 ± 0.20 | 0.74 ± 0.29 | 0.73 ± 0.30 | 0.36 ± 0.12 | 0.52 ± 0.15 |
| DD7 (epith) | 0.27 ± 0.21 | 0.99 ± 0.34 | 0.73 ± 0.24 | 0.35* ± 0.10 | 0.65 ± 0.18 | 0.51 ± 0.11 |
| DD8 (epith) | 0.70 ± 0.22 | 0.73 ± n.a. | 0.70 ± 0.17 | 0.62 ± 0.09 | 0.54 ± 0.11 | 0.58 ± 0.07 |
| DD9 (epith) | 0.76 ± 0.23 | 0.35 ± 0.06 | 0.52 ± 0.11 | 0.43* ± 0.09 | 0.40 ± 0.13 | 0.42 ± 0.08 |
| DD10 (epith) | 0.21 ± 0.06 | 0.08 n.a. | 0.18 ± 0.05 | 0.26 ± 0.03 | 0.13 ± 0.02 | 0.20 ± 0.02 |
| DD11 (biop) | | | | | | |
| DD12 (biop) | 17.10 ± 1.91 | 42.96 ± 5.10 | 20.79 ± 3.04 | 16.05 ± 1.46 | 36.67 ± 3.35 | 23.78* ± 2.35 |
| DD12 (biop NB) | 0.27 ± 0.13 | 0.53 ± 0.33 | 0.31 ± 0.12 | 0.37 ± 0.10 | 0.52 ± 0.13 | 0.42* ± 0.09 |
| DD13 (biop) | 0.87 ± 0.17 | 0.47 ± 0.11 | 0.82* ± 0.15 | 0.86 ± 0.12 | 0.28 ± 0.06 | 0.63 ± 0.09 |
| DD14 (biop) | 1.18 ± 0.15 | 2.06 ± 0.13 | 1.31 ± 0.15 | 1.77 ± 0.37 | 1.37 ± 0.18 | 1.62* ± 0.24 |
| DD15 (biop) | 0.48 ± 0.15 | 0.12 ± 0.12 | 0.39 ± 0.13 | 0.49 ± 0.09 | 0.28 ± 0.07 | 0.42* ± 0.07 |
| DD16 (biop) | 1.63 ± 0.33 | 1.90 ± 0.19 | 1.70 ± 0.24 | 0.96 ± 0.19 | 1.58 ± 0.11 | 1.19* ± 0.14 |
| HIF1α (epith) | 1.47 ± 0.33 | 2.27 n.a. | 1.62 ± 0.30 | 1.33 ± 0.12 | 1.31 ± 0.17 | 1.32* ± 0.10 |
| HIF1α (biop NB) | 1.16 ± 0.14 | 1.27 ± 0.71 | 1.19 ± 0.21 | 1.11* ± 0.10 | 1.61 ± 0.32 | 1.28 ± 0.13 |
| ARNT (epith) | 1.03 ± 0.17 | 10.13 ± 7.93 | 6.49 ± 4.80 | 1.04* ± 0.14 | 5.72 ± 3.78 | 3.44 ± 1.96 |
| AK3 (epith) | 3.16 ± 2.12 | 13.83 ± 10.70 | 8.91 ± 5.83 | 1.40 ± 0.89 | 6.78 ± 5.10 | 4.10 ± 2.59 |
| Glut-1 (epith) | 1.23 ± 0.39 | 2.33 ± 0.77 | 1.87* ± 0.49 | 0.81 ± 0.19 | 1.77 ± 0.50 | 1.26 ± 0.27 |
| MnSOD (epith) | 5.35 ± 4.12 | 6.29 ± 2.85 | 5.90 ± 2.27 | 2.81 ± 1.73 | 4.94 ± 1.77 | 4.03* ± 1.25 |
| MnSOD (biop) | 0.89 ± 0.07 | 1.36 ± 0.30 | 0.98 ± 0.29 | 0.90 ± 0.09 | 2.00 ± 0.33 | 1.30 ± 0.16 |
| GPx (epith) | 1.83 ± 0.35 | 2.80 n.a. | 2.02 0.33 | 1.57 ± 0.16 | 2.08 ± 0.18 | 1.80* ± 0.13 |
| catalase (biop) | 0.46 ± 0.18 | 0.14 n.a. | 0.41 ± 0.16 | 0.74 ± 0.18 | 0.13* ± 0.03 | 0.55 ± 0.14 |
| GST (epith) | 0.80 ± 0.48 | 0.67 ± 0.21 | 0.71 ± 0.20 | 0.35 ± 0.13 | 0.42 ± 0.13 | 0.39 ± 0.09 |
| eNOS (epith) | 0.07 ± 0.03 | 0.04 n.a. | 0.06 ± 0.02 | 0.15* ± 0.04 | 0.37 ± 0.09 | 0.24 ± 0.05 |
| CO3/DD11 (epith) | 0.35 ± 0.19 | 0.03 n.a. | 0.29 ± 0.16 | 0.47 ± 0.07 | 0.29* ± 0.07 | 0.39 ± 0.05 |
| 12S rRNA (biop) | 4.57 ± 1.83 | 1.68 n.a. | 4.16 ± 1.60 | 1.98 ± 0.74 | 2.69 ± 1.06 | 2.21 ± 0.60 |
| TI227H (biop) | 0.02 ± 0.01 | 0.05 ± 0.05 | 0.03* ± 0.01 | 0.30 ± 0.09 | 0.37 ± 0.15 | 0.33 ± 0.08 |
| CO2 (biop) | 0.83 ± 0.20 | 2.42 n.a. | 1.06 ± 0.28 | 0.37 ± 0.10 | 0.62 ± 0.23 | 0.45 ± 1.10 |
| aconitase (biop) | 0.20 ± 0.03 | 0.30 ± 0.04 | 0.22 ± 0.03 | 0.25 ± 0.04 | 0.12 ± 0.04 | 0.21 ± 0.03 |

TABLE 3-continued

Summary of average values (±SEM, standard error of the mean) by group for the endometriosis-related markers

| | | | | | | |
|---|---|---|---|---|---|---|
| ANT-1 (biop) | 0.02 ± 0.01 | 0.00 n.a. | 0.01 ± 0.005 | 0.01* ± 0.002 | 0.07 ± 0.02 | 0.03 ± 0.01 |
| ANT-1 (biop NB) | 0.02 ± 0.01 | 0.10 ± 0.06 | 0.05 ± 0.02 | 0.04* ± 0.01 | 0.05 ± 0.03 | 0.04 ± 0.01 |
| ATP synthase (biop) | 11.26 ± 2.19 | 13.14 n.a. | 11.53 ± 1.87 | 7.02 ± 1.18 | 9.85 ± 1.33 | 7.93* ± 0.93 |
| | 11.26 ± 2.19 | 13.14 n.a. | 11.53 ± 1.87 | 7.02* ± 1.18 | 9.85 ± 1.33 | 7.93 ± 0.93 |
| Bcl-2 (biop) | 0.99 ± 0.38 | 2.81 n.a. | 1.25 ± 0.41 | 3.02 ± 0.70 | 1.04 ± 0.35 | 2.38* ± 0.51 |
| c-jun (epith) | 0.63 ± 0.31 | 0.10 n.a. | 0.50 ± 0.26 | 0.55 ± 0.09 | 0.77 ± 0.12 | 0.64 ± 0.08 |
| c-jun (biop) | 1.35 ± 0.21 | 1.55 ± 0.45 | 1.38 ± 0.18 | 1.19 ± 0.16 | 1.78 ± 0.32 | 1.38* ± 0.16 |
| COUP-TF (biop) | 0.10 ± 0.06 | 0.12 n.a. | 0.10 ± 0.05 | 0.09 ± 0.03 | 0.07* ± 0.02 | 0.08 ± 0.02 |
| IL-1β (epith) | 0.31 ± 0.15 | 0.06 n.a. | 0.25* ± 0.12 | 1.13 ± 0.31 | 1.05 ± 0.27 | 1.10 ± 0.21 |
| Cx43 (epith) | 1.30 ± 0.27 | 0.26 n.a. | 1.04 ± 0.32 | 1.61 ± 0.18 | 0.98 ± 0.18 | 1.33 ± 0.14 |
| | 1.30 ± 0.27 | 0.26 n.a. | 1.04 ± 0.32 | 1.61 ± 0.18 | 0.98 ± 0.18 | 1.33 ± 0.14 |
| HSP 70 (epith) | 2.61 ± 1.01 | 2.75 ± 1.67 | 2.70 ± 1.10 | 1.50 ± 0.38 | 1.78 ± 0.81 | 1.65* ± 0.46 |
| HSP 70 (biop) | 1.06 ± 0.33 | 0.10 n.a. | 0.99 ± 0.31 | 0.96* ± 0.22 | 0.71 ± 0.28 | 0.89 ± 0.18 |
| HSP 90 (epith) | 0.05 ± 0.02 | n.a. n.a. | 0.05* ± 0.02 | 0.30 ± 0.06 | 0.19 ± 0.03 | 0.25 ± 0.04 |
| GPx4 (biop) | 0.09 ± 0.02 | 0.81 n.a. | 0.19 ± 0.10 | 0.07 ± 0.01 | 0.15 ± 0.08 | 0.10 ± 0.03 |
| GRP78 (biop) | 1.66 ± 0.41 | 4.60 n.a. | 2.08 ± 0.54 | 4.97 ± 1.08 | 1.96* ± 0.71 | 3.10 ± 0.80 |
| cox2 (biop) | 2.67 ± 0.79 | 3.75 n.a. | 2.83 ± 0.68 | 7.20 ± 1.53 | 9.07 ± 2.65 | 7.80 ± 1.33 |

TABLE 4

Overexpressed endometriosis-related markers

| Name | Specificity | Sensitivity | Modulated phase | Modulated EXP group | Significance (p value)* |
|---|---|---|---|---|---|
| DD9 (epith) | 70% | 70% | ↑ P¤¤ | 1&2 | 0.008 |
| DD10 (epith) | 71% | 71% | ↑ P | 1 | 0.04 |
| DD13 (biop) | 62% | 64% | ↑ P&S¤ | 2 | 0.04 |
| DD14 (biop) | 78% | 58% | ↑ P&S | 1&2 | 0.04 |
| DD15 (biop) | 85% | 79% | ↑ P&S | 1&2 | 0.0006 |
| HIF1α (epith) | 65% | 72% | ↑ P&S | 1&2 | 0.028 |
| HIF1α (biop NB) | 83% | 80% | ↑ P | 1&2 | 0.019 |
| ARNT (epith) | 67% | 83% | ↑ P | 1&2 | 0.02 |
| Glut-1 (epith) | 71% | 67% | ↑ P&S | 2 | 0.037 |
| MnSOD (epith) | 76% | 58% | ↑ P&S | 1&2 | 0.017 |
| MnSOD (biop) | 81% | 53% | ↑ P&S | 1&2 | 0.003 |
| GPx (epith) | 100% | 87.5% | ↑P&S | 1&2 | $1.7 \times 10^{-11}$ |
| ATP synthase (biop) | 77% | 75% | ↑ P&S | 1&2 | $10^{-3}$ |
| | 93% | 64% | ↑ P | 1&2 | $8 \times 10^{-4}$ |
| c-jun (epith) | 75% | 67% | ↑ S | 1 | 0.05 |
| c-jun (biop) | 76% | 65% | ↑ P&S | 1&2 | 0.005 |
| Cx43 (epith) | 74% | 48% | ↑ P&S | 1 | 0.048 |
| | 77% | 64% | ↑ P | 1 | 0.02 |
| HSP 70 (epith) | 73% | 61% | ↑ P&S | 1&2 | 0.01 |
| HSP 70 (biop) | 71% | 78% | ↑ P | 1&2 | 0.014 |
| cox2 (biop) | 69% | 62% | ↑ P&S | 1 | 0.01 |

TABLE 5

Underexpressed endometriosis-related markers

| Name | Specificity | Sensitivity | Modulated phase | Modulated EXP group | Significance (p value)* |
|---|---|---|---|---|---|
| DD1 (epith) | 75% | 90% | ↓ S¤ | 1 | 0.01 |
| DD2 (epith) | 65% | 77% | ↓ P¤¤&S | 1&2 | 0.04 |
| DD3 (epith) | 63% | 69% | ↓ P&S | 1&2 | 0.01 |
| DD4 (epith) | 83% | 85% | ↓ S | 1&2 | 0.04 |
| DD5 (epith) | 78% | 79% | ↓ P | 1&2 | 0.03 |
| DD5 | 77% | 61% | ↓ S | 1&2 | 0.001 |
| (biop PROT)+ | 71% | 57% | ↓ S | 1&2 | 0.05 |
| DD6 (epith) | 89% | 100% | ↓ S | 1 | 0.018 |
| DD7 (epith) | 80% | 70% | ↓ P | 1&2 | 0.019 |
| DD8 (epith) | 67% | 60% | ↓ P&S | 1 | 0.02 |
| DD12 (biop) | 81% | 56% | ↓ P&S | 1&2 | 0.015 |
| DD12 (biop NB) | 55% | 68% | ↓ P&S | 1&2 | 0.05 |
| DD16 (biop) | 70% | 78% | ↓ P&S | 1&2 | $3.5 \times 10^{-5}$ |
| AK3 (epith) | 68% | 82% | ↓ P&S | 1 | 0.005 |
| catalase (biop) | 83% | 78% | ↓ S | 1&2 | 0.001 |
| GST (epith) | 54% | 74% | ↓ P&S | 1 | 0.026 |
| eNOS (epith) | 77% | 65% | ↓ P | 1&2 | 0.027 |
| CO3/DD11 (epith) | 83% | 79% | ↓ S | 1&2 | 0.002 |
| 12S rRNA (biop) | 77% | 67% | ↓ P&S | 1 | 0.02 |
| TI227H (biop) | 81% | 100% | ↓ P&S | 2 | $2 \times 10^{-8}$ |
| CO2 (biop) | 64% | 69% | ↓ P | 1 | 0.02 |
| aconitase (biop) | 80% | 86% | ↓ S | 1 | 0.005 |
| ANT-1 (biop) | 86% | 74% | ↓ P | 1&2 | 0.007 |
| ANT-1 (biop NB) | 75% | 73% | ↓ P | 1&2 | 0.016 |
| Bcl-2 (biop) | 54% | 82% | ↓ P&S | 1&2 | 0.01 |
| COUP-TF (biop) | 83% | 78% | ↓ S | 1&2 | 0.01 |
| IL-1β (epith) | 78% | 100% | ↓ P&S | 2 | 0.0002 |
| HSP 90 (epith) | 75% | 100% | ↓ P&S | 2 | $4.3 \times 10^{-5}$ |
| GPx4 (biop) | 83% | 75% | ↓ S | 1 | $5 \times 10^{-3}$ |
| GRP78 (biop) | 92% | 78% | ↓ S | 1&2 | $6 \times 10^{-3}$ |

TABLE 6

Endometriosis-related markers modulated in the proliferative phase

| Name | Specificity | Sensitivity | Modulated phase | Modulated EXP group | Significance (p value)* |
|---|---|---|---|---|---|
| DD5 (epith) | 78% | 79% | ↓ P¤¤ | 1&2 | 0.03 |
| DD7 (epith) | 80% | 70% | ↓ P | 1&2 | 0.019 |
| DD9 (epith) | 70% | 70% | ↑ P | 1&2 | 0.008 |
| DD10 (epith) | 71% | 71% | ↑ P | 1 | 0.04 |
| HIF1α (biop NB) | 83% | 80% | ↑ P | 1&2 | 0.019 |
| ARNT (epith) | 67% | 83% | ↑ P | 1&2 | 0.02 |
| eNOS (epith) | 77% | 65% | ↓ P | 1&2 | 0.027 |
| CO2 (biop) | 64% | 69% | ↓ P | 1 | 0.02 |
| ANT-1 (biop) | 86% | 74% | ↓ P | 1&2 | 0.007 |
| ATP synthase (biop) | 93% | 64% | ↑ P | 1&2 | $8 \times 10^{-4}$ |
| Cx43 (epith) | 77% | 64% | ↑ P | 1 | 0.02 |
| HSP 70 (biop) | 71% | 78% | ↑ P | 1&2 | 0.014 |
| DD2 (epith) | 65% | 77% | ↓ P&S¤ | 1&2 | 0.04 |
| DD3 (epith) | 63% | 69% | ↓ P&S | 1&2 | 0.01 |
| DD8 (epith) | 67% | 60% | ↓ P&S | 1 | 0.02 |
| DD12 (biop) | 81% | 56% | ↓ P&S | 1&2 | 0.015 |
| DD12 (biop NB) | 55% | 68% | ↓ P&S | 1&2 | 0.05 |
| DD13 (biop) | 62% | 64% | ↑ P&S | 2 | 0.04 |
| DD14 (biop) | 78% | 58% | ↑ P&S | 1&2 | 0.04 |
| DD15 (biop) | 85% | 79% | ↑ P&S | 1&2 | 0.0006 |
| DD16 (biop) | 70% | 78% | ↓ P&S | 1&2 | $3.5 \times 10^{-5}$ |
| HIF1α (epith) | 65% | 72% | ↑ P&S | 1&2 | 0.028 |
| AK3 (epith) | 68% | 82% | ↓ P&S | 1 | 0.005 |
| Glut-1 (epith) | 71% | 67% | ↑ P&S | 2 | 0.037 |
| MnSOD (epith) | 76% | 58% | ↑ P&S | 1&2 | 0.017 |
| MnSOD (biop) | 81% | 53% | ↑ P&S | 1&2 | 0.003 |
| GPx (epith) | 100% | 87.5% | ↑P&S | 1&2 | $1.7 \times 10^{-11}$ |
| GST (epith) | 54% | 74% | ↓ P&S | 1 | 0.026 |
| 12S rRNA (biop) | 77% | 67% | ↓ P&S | 1 | 0.02 |
| TI227H (biop) | 81% | 100% | ↓ P&S | 2 | $2 \times 10^{-8}$ |
| ANT-1 (biop NB) | 85% | 75% | ↓ P&S | 1&2 | 0.016 |
| ATP synthase (biop) | 77% | 75% | ↑ P&S | 1&2 | $10^{-3}$ |
| Bcl-2 (biop) | 54% | 82% | ↓ P&S | 1&2 | 0.01 |
| c-jun (biop) | 76% | 65% | ↑ P&S | 1&2 | 0.005 |
| IL-1β (epith) | 78% | 100% | ↓ P&S | 2 | 0.0002 |
| Cx43 (epith) | 74% | 48% | ↑ P&S | 1 | 0.048 |
| HSP 70 (epith) | 73% | 61% | ↑ P&S | 1&2 | 0.01 |
| HSP 90 (epith) | 75% | 100% | ↓ P&S | 2 | $4.3 \times 10^{-5}$ |
| cox2 (biop) | 69% | 62% | ↑ P&S | 1 | 0.01 |

TABLE 7

Endometriosis-related markers modulated in the secretory phase

| Name | Specificity | Sensitivity | Modulated phase | Modulated EXP group | Significance (p value)* |
|---|---|---|---|---|---|
| DD1 (epith) | 75% | 90% | ↓ S¤ | 1 | 0.01 |
| DD4 (epith) | 83% | 85% | ↓ S | 1&2 | 0.04 |
| DD6 (epith) | 89% | 100% | ↓ S | 1 | 0.018 |
| catalase (biop) | 83% | 78% | ↓ S | 1&2 | 0.001 |
| CO3/DD11 (epith) | 83% | 79% | ↓ S | 1&2 | 0.002 |
| aconitase (biop) | 80% | 86% | ↓ S | 1 | 0.005 |
| c-jun (epith) | 75% | 67% | ↑ S | 1 | 0.05 |
| COUP-TF (biop) | 83% | 78% | ↓ S | 1&2 | 0.01 |
| GPx4 (biop) | 83% | 75% | ↓ S | 1 | $5 \times 10^{-3}$ |
| GRP78 (biop) | 92% | 78% | ↓ S | 1&2 | $6 \times 10^{-3}$ |
| DD2 (epith) | 65% | 77% | ↓ P¤¤&S | 1&2 | 0.04 |
| DD3 (epith) | 63% | 69% | ↓ P&S | 1&2 | 0.01 |
| DD8 (epith) | 67% | 60% | ↓ P&S | 1 | 0.02 |
| DD12 (biop) | 81% | 56% | ↓ P&S | 1&2 | 0.015 |
| DD12 (biop NB) | 55% | 68% | ↓ P&S | 1&2 | 0.05 |
| DD13 (biop) | 62% | 64% | ↑ P&S | 2 | 0.04 |
| DD14 (biop) | 78% | 58% | ↑ P&S | 1&2 | 0.04 |
| DD15 (biop) | 85% | 79% | ↑ P&S | 1&2 | 0.0006 |
| DD16 (biop) | 70% | 78% | ↓ P&S | 1&2 | $3.5 \times 10^{-5}$ |
| HIF1α (epith) | 65% | 72% | ↑ P&S | 1&2 | 0.028 |
| AK3 (epith) | 68% | 82% | ↓ P&S | 1 | 0.005 |
| Glut-1 (epith) | 71% | 67% | ↑ P&S | 2 | 0.037 |
| MnSOD (epith) | 76% | 58% | ↑ P&S | 1&2 | 0.017 |
| MnSOD (biop) | 81% | 53% | ↑ P&S | 1&2 | 0.003 |
| GPx (epith) | 100% | 87.5% | ↑P&S | 1&2 | $1.7 \times 10^{-11}$ |
| GST (epith) | 54% | 74% | ↓ P&S | 1 | 0.026 |
| 12S rRNA (biop) | 77% | 67% | ↓ P&S | 1 | 0.02 |
| TI227H (biop) | 81% | 100% | ↓ P&S | 2 | $2 \times 10^{-8}$ |
| ANT-1 (biop NB) | 85% | 75% | ↓ P&S | 1&2 | 0.016 |
| ATP synthase (biop) | 77% | 75% | ↑ P&S | 1&2 | $10^{-3}$ |
| Bcl-2 (biop) | 54% | 82% | ↓ P&S | 1&2 | 0.01 |
| c-jun (biop) | 76% | 65% | ↑ P&S | 1&2 | 0.005 |
| IL-1β (epith) | 78% | 100% | ↓ P&S | 2 | 0.0002 |
| Cx43 (epith) | 74% | 48% | ↑ P&S | 1 | 0.048 |
| HSP 70 (epith) | 73% | 61% | ↑ P&S | 1&2 | 0.01 |
| HSP 90 (epith) | 75% | 100% | ↓ P&S | 2 | $4.3 \times 10^{-5}$ |
| cox2 (biop) | 69% | 62% | ↑ P&S | 1 | 0.01 |

TABLE 8

Endometriosis-related markers modulated according to the stage of the disease

| Name | Specificity | Sensitivity | Modulated phase | Modulated EXP group | Significance (p value)* |
|---|---|---|---|---|---|
| DD1 (epith) | 75% | 90% | ↓ S¤ | 1 | 0.01 |
| DD6 (epith) | 89% | 100% | ↓ S | 1 | 0.018 |
| DD8 (epith) | 67% | 60% | ↓ P¤¤&S | 1 | 0.02 |
| DD10 (epith) | 71% | 71% | ↑ P | 1 | 0.04 |
| AK3 (epith) | 68% | 82% | ↓ P&S | 1 | 0.005 |
| GST (epith) | 54% | 74% | ↓ P&S | 1 | 0.026 |
| 12S rRNA (biop) | 77% | 67% | ↓ P&S | 1 | 0.02 |
| CO2 (biop) | 64% | 69% | ↓ P | 1 | 0.02 |
| aconitase (biop) | 80% | 86% | ↓ S | 1 | 0.005 |
| c-jun (epith) | 75% | 67% | ↑ S | 1 | 0.05 |
| Cx43 (epith) | 74% | 48% | ↑ P&S | 1 | 0.048 |
| | 77% | 64% | ↑ P | 1 | 0.02 |
| GPx4 (biop) | 83% | 75% | ↓ S | 1 | $5 \times 10^{-3}$ |
| cox2 (biop) | 69% | 62% | ↑ P&S | 1 | 0.01 |
| DD13 (biop) | 62% | 64% | ↑ P&S | 2 | 0.04 |
| Glut-1 (epith) | 71% | 67% | ↑ P&S | 2 | 0.037 |
| TI227H (biop) | 81% | 100% | ↓ P&S | 2 | $2 \times 10^{-8}$ |
| IL-1β (epith) | 78% | 100% | ↓ P&S | 2 | 0.0002 |
| HSP 90 (epith) | 75% | 100% | ↓ P&S | 2 | $4.3 \times 10^{-5}$ |

TABLE 9

Endometriosis-related markers overexpressed in stage I or II (EXP 1), or in stage III or IV (EXP 2) the disease

| Name | Specificity | Sensitivity | Modulated phase | Modulated EXP group | Significance (p value)* |
|---|---|---|---|---|---|
| DD10 (epith) | 71% | 71% | ↑ P | 1 | 0.04 |
| c-jun (epith) | 75% | 67% | ↑ S | 1 | 0.05 |
| Cx43 (epith) | 74% | 48% | ↑ P&S | 1 | 0.048 |
|  | 77% | 64% | ↑ P | 1 | 0.02 |
| cox2 (biop) | 69% | 62% | ↑ P&S | 1 | 0.01 |
| DD13 (biop) | 62% | 64% | ↑ P&S | 2 | 0.04 |
| Glut-1 (epith) | 71% | 67% | ↑ P&S | 2 | 0.037 |

TABLE 10

Endometriosis-related markers underexpressed in stage I or II (EXP 1), or in stage III or IV (EXP 2) of the disease

| Name | Specificity | Sensitivity | Modulated phase | Modulated EXP group | Significance (p value)* |
|---|---|---|---|---|---|
| CO2 (biop) | 64% | 69% | ↓ P | 1 | 0.02 |
| DD1 (epith) | 75% | 90% | ↓ S¤ | 1 | 0.01 |
| DD6 (epith) | 89% | 100% | ↓ S | 1 | 0.018 |
| aconitase (biop) | 80% | 86% | ↓ S | 1 | 0.005 |
| GPx4 (biop) | 83% | 75% | ↓ S | 1 | $5 \times 10^{-3}$ |
| DD8 (epith) | 67% | 60% | ↓ P¤¤&S | 1 | 0.02 |
| AK3 (epith) | 68% | 82% | ↓ P&S | 1 | 0.005 |
| GST (epith) | 54% | 74% | ↓ P&S | 1 | 0.026 |
| 12S rRNA (biop) | 77% | 67% | ↓ P&S | 1 | 0.02 |
| TI227H (biop) | 81% | 100% | ↓ P&S | 2 | $2 \times 10^{-8}$ |
| IL-1β (epith) | 78% | 100% | ↓ P&S | 2 | 0.0002 |
| HSP 90 (epith) | 75% | 100% | ↓ P&S | 2 | $4.3 \times 10^{-5}$ |

Legend for Tables 3 to 10:
CTL: Control group (endometriosis-free women)
ENDO: Endo group (women having endometriosis)
EXP: Refer to the Endo group: EXP1: women at stages I and II of the disease
EXP2: women stages III and IV of the disease
epith: marker derived from epithelial cell RNA
biop: marker derived from unfractioned biopsy RNA
biop PROT+: marker derived from unfractioned biopsy protein
*: indicates a significant difference according to the Student t test of the compared groups described
¤ S: secretory phase
¤¤ P: proliferative phase
NB: indicates marker derived from unfractioned biopsy RNA obtained by northern blot analysis
n.a.: not available

TABLE 11

Combinations of genetic endometriosis-related markers

|  |  | Specificity | Sensitivity |
|---|---|---|---|
| Individual markers alone | GRP 78 | 92% | 78% |
|  | Catalase | 83% | 78% |
|  | COUP-TF | 83% | 78% |
| Combination of 2 markers | GRP 78 & catalase | 75% | 100% |
|  | GRP 78 & COUP-TF | 75% | 89% |
|  | Catalase & COUP-TF | 75% | 100% |
| Combination of 3 markers | GRP 78 & catalase & COUP-TF | 92% | 89% |

While several embodiments of the invention have been described, it will be understood that the present invention is capable of further modifications, and this application is intended to cover any variations, uses, or adaptations of the invention, following in general the principles of the invention and including such departures from the present disclosure as to come within knowledge or customary practice in the art to which the invention pertains, and as may be applied to the essential features hereinbefore set forth and falling within the scope of the invention or the limits of the appended claims.

What is claimed is:

1. A method for determining the likelihood of endometriosis in a female subject, comprising the steps of: obtaining a sample of endometrial cells from said female subject; assaying said endometrial cells sample for the expression level of at least one endometriosis-related marker, said marker being a protein encoded by the gene of CAP43 or fragments of said protein which are immunoreactive to CAP43 antibodies, whereby the expression level of said at least one endometriosis-related marker being indicative of the likelihood of endometriosis in said female subject.

2. The method of claim 1 wherein said endometriosis-related marker is a protein expressed by the polynucleotide having the sequence SEQ ID NO: 5 or fragments of said protein which are immunoreactive to CAP43 antibodies.

3. A method for determining the likelihood of endometriosis in a female subject, comprising the steps of: obtaining a sample of endometrial cells from said female subject; assaying said endometrial cells sample for the expression level of at least one endometriosis-related marker, said marker being the protein expressed by the polynucleotide having the sequence of SEQ ID NO: 5, the expression level of said at least one endometriosis-related marker being indicative of the likelihood of endometriosis in said female subject.

* * * * *

SEQUENCE LISTING

```
<160> NUMBER OF SEQ ID NOS: 16

<210> SEQ ID NO 1
<211> LENGTH: 231
<212> TYPE: DNA
<213> ORGANISM: Homo sapiens

<400> SEQUENCE: 1
ggttagtaat tctgcagatc gctagctcga cgattcattg gctgaatagc cagtggtgca      60
ggacatatgc acagtgtctg acctcagtaa cttcactctc atacatatgt attaggacac     120
caacacatgt gtgcatataa gatgtatgat agatattgca acaagtaata atttactgtc     180
ctatttatag gattttaaac ttaaactact ttcaccctat ttccaaaaaa a              231

<210> SEQ ID NO 2
<211> LENGTH: 174
<212> TYPE: DNA
<213> ORGANISM: Homo sapiens
<220> FEATURE:
<221> NAME/KEY: misc_feature
<222> LOCATION: (53)..(53)
<223> OTHER INFORMATION: n = A, C, G, or T

<400> SEQUENCE: 2
```

-continued

```
gactgtactg aaagggccaa gagtaaatgc cttcgttttg ttttttttcgt ttnttttgtt      60 ttagctttt  gttaaaacgt ctatagattg gcagttaatg ctgaatttgt caaataccc       120 ttccaaaatt atactttgta tttaaaaaat aaatgggatc tacctaattt ccaa            174
```

<210> SEQ ID NO 3
<211> LENGTH: 123
<212> TYPE: DNA
<213> ORGANISM: Homo sapiens
<220> FEATURE:
<221> NAME/KEY: misc_feature
<222> LOCATION: (11)..(11)
<223> OTHER INFORMATION: n = A, C, G, or T

<400> SEQUENCE: 3

```
cgactgtatg ntgaacgtag gtgcgataaa taataggatc gaggcaggaa tcaaagacag      60
atactgcgac atagggtgct ccggctccag cgtctcgcaa tgctatcgcg tgcataccc       120 caa                                                                    123
```

<210> SEQ ID NO 4
<211> LENGTH: 108
<212> TYPE: DNA
<213> ORGANISM: Homo sapiens

<400> SEQUENCE: 4

```
cgactgtgga cgagagggaa cctggtggtg ggaccatgga ggcagggtgc agaggtgcac      60
aataaaattg attatcatcg tttttgagaa tgttgttggt ttccccca                   108
```

<210> SEQ ID NO 5
<211> LENGTH: 297
<212> TYPE: DNA
<213> ORGANISM: Homo sapiens
<220> FEATURE:
<221> NAME/KEY: misc_feature
<222> LOCATION: (85)..(85)
<223> OTHER INFORMATION: n = A, C, G, or T
<220> FEATURE:
<221> NAME/KEY: misc_feature
<222> LOCATION: (237)..(237)
<223> OTHER INFORMATION: n = A, C, G, or T

<400> SEQUENCE: 5

```
aagctttggt cagagtgaat tgaatattgt aagtcagcca ctgggacccg aggattctgg      60
gaccccgcag ttgggaggag gaatnagtcc agccttccag gtggcgtgag aggcaatgac     120
tcgttacctg ccgcccatca ccttggaggc cttccctggc cttgagtaga aaagtcgggg     180
atcggggcaa gagaggctga gtacggatgg gaaactattg tgcacaagtc tttccanagg     240
agtttcttaa tgagagtttg tatttatttc cagaccaata aatttgtaac tttgcaa        297
```

<210> SEQ ID NO 6
<211> LENGTH: 184
<212> TYPE: DNA
<213> ORGANISM: Homo sapiens
<220> FEATURE:
<221> NAME/KEY: misc_feature
<222> LOCATION: (55)..(55)
<223> OTHER INFORMATION: n = A, C, G, or T
<220> FEATURE:
<221> NAME/KEY: misc_feature
<222> LOCATION: (63)..(63)
<223> OTHER INFORMATION: n = A, C, G, or T
<220> FEATURE:
<221> NAME/KEY: misc_feature
<222> LOCATION: (68)..(68)
<223> OTHER INFORMATION: n = A, C, G, or T -continued

```
<400> SEQUENCE: 6
aagctttggt cagggataga gaatgaaagt gagatcattt agatcttaga aaggnagatg     60
ttnggctngg gcacggtggc tcacacctgt aatcccagca cttgggaagc catggtgggc    120
agatcatttg agctcaggag tttgcaacca gcctgggcaa tatggcaaga ccccatctgt    180
acaa                                                                  184

<210> SEQ ID NO 7
<211> LENGTH: 143
<212> TYPE: DNA
<213> ORGANISM: Homo sapiens

<400> SEQUENCE: 7
ttgtattttt agtaaagacg gggtttcact atgttggcca ggctggtctc gaactcctga     60
cctcgtgatc cacccacctt ggcctcccaa tcttatttgc tttacaagtc ctgcttcagg    120
gttaccttcc ctgaccaaag ctt                                             143

<210> SEQ ID NO 8
<211> LENGTH: 319
<212> TYPE: DNA
<213> ORGANISM: Homo sapiens
<220> FEATURE:
<221> NAME/KEY: misc_feature
<222> LOCATION: (259)..(259)
<223> OTHER INFORMATION: n = A, C, G, or T
<220> FEATURE:
<221> NAME/KEY: misc_feature
<222> LOCATION: (269)..(269)
<223> OTHER INFORMATION: n = A, C, G, or T
<220> FEATURE:
<221> NAME/KEY: misc_feature
<222> LOCATION: (290)..(290)
<223> OTHER INFORMATION: n = A, C, G, or T
<220> FEATURE:
<221> NAME/KEY: misc_feature
<222> LOCATION: (302)..(302)
<223> OTHER INFORMATION: n = A, C, G, or T
<220> FEATURE:
<221> NAME/KEY: misc_feature
<222> LOCATION: (306)..(306)
<223> OTHER INFORMATION: n = A, C, G, or T

<400> SEQUENCE: 8
tctaatgcat aataaaatga aaggaatcgt aaaacagttt cgttccaaaa agtcagagat     60
aaagactatc catgaaggtt cacttttgag gcaagaaccc ttttttatgc aagactatgt    120
ggcatcagaa aactaaaatg tgattccacca acatgccagc caatgttcat taaaaatctg   180
tcccttacta acaggtgcaa cagcgaccgg gaacatcacc ttacacagta taacgtggaa    240
agaaaagaca acattgggng cacttctcnt ctccaaaacc ttatctttcn attcagcttt    300
ancatntact gcaggactg                                                 319

<210> SEQ ID NO 9
<211> LENGTH: 277
<212> TYPE: DNA
<213> ORGANISM: Homo sapiens
<220> FEATURE:
<221> NAME/KEY: misc_feature
<222> LOCATION: (50)..(50)
<223> OTHER INFORMATION: n = A, C, G, or T

<400> SEQUENCE: 9
ttgattcggt tcagtctaat ccttttttgta tcactcatag gccagacttn agggctagga    60
tgatgattaa taagagggat gacataacta ttagtggcag gtagttgttt gtagggctca   120
```

```
tggtaggggt aaaaggaggg caatttctag atcaaataat aagaaggtaa tagctactaa      180 gaagaattttt atggagaaag ggacgcgggc gggggtatata gggtcgaagc cgcactcgta    240
aggggtggat ttttctatgt agccgttgaa gaagctt                              277
```

```
<210> SEQ ID NO 10
<211> LENGTH: 320
<212> TYPE: DNA
<213> ORGANISM: Homo sapiens
<220> FEATURE:
<221> NAME/KEY: misc_feature
<222> LOCATION: (48)..(48)
<223> OTHER INFORMATION: n = A, C, G, or T
<220> FEATURE:
<221> NAME/KEY: misc_feature
<222> LOCATION: (284)..(284)
<223> OTHER INFORMATION: n = A, C, G, or T
<220> FEATURE:
<221> NAME/KEY: misc_feature
<222> LOCATION: (287)..(287)
<223> OTHER INFORMATION: n = A, C, G, or T
<220> FEATURE:
<221> NAME/KEY: misc_feature
<222> LOCATION: (311)..(311)
<223> OTHER INFORMATION: n = A, C, G, or T

<400> SEQUENCE: 10
gtaggcagtt gaggtggatt aaaccaaacc cagctacgca aaatcctnag catactcctc       60
aattacccac ataggatgaa taatagcagt tctaccgtac aaccctaaca taacctgctt     120
aatttaacta tttatattat cctaactact accgcattcc tactactcaa cttaaactcc     180
agcaccacga ccctactact atctcgcacc tgtaacaagc taacatgact aacacccttta    240 attccatcca ccctcctctc cctaggaggc ctgaccccgc taancgngct ttttgcccaa     300
ttgggcatta ncgagattca                                                 320
```

```
<210> SEQ ID NO 11
<211> LENGTH: 327
<212> TYPE: DNA
<213> ORGANISM: Homo sapiens
<220> FEATURE:
<221> NAME/KEY: misc_feature
<222> LOCATION: (58)..(58)
<223> OTHER INFORMATION: n = A, C, G, or T
<220> FEATURE:
<221> NAME/KEY: misc_feature
<222> LOCATION: (101)..(101)
<223> OTHER INFORMATION: n = A, C, G, or T
<220> FEATURE:
<221> NAME/KEY: misc_feature
<222> LOCATION: (324)..(324)
<223> OTHER INFORMATION: n = A, C, G, or T

<400> SEQUENCE: 11
gtaggcctaa aagcagccac caattaagaa agcgttcaag ctcaacaccc actacctnaa       60 aaatcccaa acatataact gaactcctca cacccaattg ngaccaatct atcccctat       120 agaagaacta atgttagtat aagtaacatg aaaacattct cctccgcata agccttgcgt     180
cagattaaaa cactgaactg acaattaaca gcccaatatc tacaatcaac caacaagtca     240
ttattaccct cactgtcaac ccaacacagg catgctcata aggaaaggtt aaaaaaagta     300
aaaggaactc ggcaaatctt accncgc                                         327
```

```
<210> SEQ ID NO 12
<211> LENGTH: 254
<212> TYPE: DNA
<213> ORGANISM: Homo sapiens
```

-continued

<400> SEQUENCE: 12

```
gactgtgaca tggaatccat cattcggaat gacctcatgg atggagatac attggatttt      60
aactttgaca atgtgttgcc caaccaaagc ttcccacaca gtgtcaagac aacgacacat     120
agctgggtgt caggctgagg gttagtgagc aggttacact taaaagtact tcagattgtc     180
tgacagcagg aactgagaga agcagtccaa agatgtcttt caccaactcc cttttagttt     240
tcttggttaa aaaa                                                       254
```

<210> SEQ ID NO 13
<211> LENGTH: 295
<212> TYPE: DNA
<213> ORGANISM: Homo sapiens

<400> SEQUENCE: 13

```
ggttgagttt gtccattgct agggagagac ttccagtaat aaaatttact attctagatg      60
cttctactgt tatgttttat ctacccattt atctttctta gttaccagga gaaatgtgtg     120
acacctatat tataatgaaa acaatcttat tacttatagt ttatctatat aaacaaatt      180
taattgcatt taaagcattc tttgatattg ttgcttttgc aataaatatg gataatcttg     240
gttataaggg agttaaaaca atgctgtaat aaataaagtg tttcatgtga tcaaa          295
```

<210> SEQ ID NO 14
<211> LENGTH: 218
<212> TYPE: DNA
<213> ORGANISM: Homo sapiens
<220> FEATURE:
<221> NAME/KEY: misc_feature
<222> LOCATION: (24)..(25)
<223> OTHER INFORMATION: n = A, C, G, or T

<400> SEQUENCE: 14

```
ttcatcatct tcttttcct catnnatctc cttccttaac ctagaaggta tgtaggactt       60
tggaaggtca gggatattag catagatgtc ctcaattgac tcttctgctc tttcttctct    120
ttccactttc acagatctta taatgtcttc tgttgtccgc tcaattgact ttagtttctt    180
taaaatggcc tcttccttcg ttgagaagct taagccga                            218
```

<210> SEQ ID NO 15
<211> LENGTH: 150
<212> TYPE: DNA
<213> ORGANISM: Homo sapiens

<400> SEQUENCE: 15

```
ggcctggctt caccgcattc caggctgcag cccctgctt ctcccgccat tgccttaact       60
gccctcgggc cctctctccg ccccggacag ggtggcaccc accactctca ggaccaccct    120
gccaaggcag aataaaccgg atcctgttgc                                      150
```

<210> SEQ ID NO 16
<211> LENGTH: 132
<212> TYPE: DNA
<213> ORGANISM: Homo sapiens

<400> SEQUENCE: 16

```
aagcttgcac catgacctaa cgttttatgt aaatacttgt gtttagtacc ttttaaggtt      60
ttgcagaaga tggcggtgta taggctgaat tagcaagaga tagtgaggtt tactggggtt    120
tattgattca aa                                                        132
```